US012759990B2

(12) United States Patent
Albeck et al.

(10) Patent No.: US 12,759,990 B2
(45) Date of Patent: Oct. 13, 2026

(54) THC DERIVATIVES, ORAL DOSAGE FORMS COMPRISING SAME, USES THEREOF FOR TREATING DISEASES AND DISORDERS AND SYNTHESIS THEREOF

(71) Applicants: BAR-ILAN UNIVERSITY, Ramat Gan (IL); Eybna Technologies Ltd., Givat Hen (IL)

(72) Inventors: Amnon Albeck, Gimzo (IL); Jacob Wolfman, Petah Tikva (IL); Nadav Eyal, Ramat Hasharon (IL)

(73) Assignees: BAR-ILAN UNIVERSITY, Ramat Gan (IL); Eybna Technologies Ltd., Givat Hen (IL)

( * ) Notice: Subject to any disclaimer, the term of this patent is extended or adjusted under 35 U.S.C. 154(b) by 449 days.

(21) Appl. No.: 18/140,303

(22) Filed: Apr. 27, 2023

(65) Prior Publication Data

US 2023/0331690 A1 Oct. 19, 2023

Related U.S. Application Data

(63) Continuation of application No. PCT/IL2021/051279, filed on Oct. 28, 2021.

(60) Provisional application No. 63/108,385, filed on Nov. 1, 2020.

(51) Int. Cl.

| | |
|---|---|
| ***C07D 311/80*** | (2006.01) |
| ***A61K 9/00*** | (2006.01) |
| ***A61P 25/04*** | (2006.01) |

(52) U.S. Cl.

CPC .......... *C07D 311/80* (2013.01); *A61K 9/0053* (2013.01); *A61P 25/04* (2018.01)

(58) Field of Classification Search

CPC .................................................. C07D 311/80

See application file for complete search history.

(56) References Cited

U.S. PATENT DOCUMENTS

| | | | | |
|---|---|---|---|---|
| 7,449,589 | B2 | 11/2008 | Geiser et al. | |
| 2010/0152283 | A1* | 6/2010 | Gant | A61K 31/352 549/390 |

FOREIGN PATENT DOCUMENTS

| | | | |
|---|---|---|---|
| WO | 02096899 | A1 | 12/2002 |
| WO | 2019023751 | A1 | 2/2019 |
| WO | 2021046636 | A1 | 3/2021 |

OTHER PUBLICATIONS

Evans et al (1999) Bis(oxazoline) and Bis(oxozolinyl pyridine Copper Complexes as Enantioselective Diels-Alder Catalysts: Reaction Scope and Synthetic Applications, J. Am. Chem. Soc. 121:7582-7594. doi: 10.1021/ja991191c.

Martin et al (1974) Marihuana-like Activity of New Synthetic Tetrahydrocannabinols, Pharmacology, Biochemistry & Behavior, 3:849-853. https://doi.org/10.1016/0091-3057(75)90116-1.

Park et al (2001) Metabolism of Fluorine-Containing Drugs, Annu. Rev. Toxicol. 41:443-70. DOI: 10.1146/annurev.pharmtox.41.1.443.

Diana et al (1995) Picornavirus Inhibitors: Trifluoromethyl Substitution Provides a Global Protective Effect against Hepatic Metabolism, J. Med. Chem. 38:1355-1371. DOI: 10.1021/jm00008a014.

PCT International Search Report for International Application No. PCT/IL2021/051279, mailed Feb. 6, 2022, 4pp.

PCT Written Opinion for International Application No. PCT/IL2021/051279, mailed Feb. 6, 2022, 8pp.

PCT International Preliminary Report on Patentability for International Application No. PCT/IL2021/051279, issued May 2, 2023, 9pp.

Usami, Noriyuki, et al. "Synthesis and pharmacological activities in mice of halogenated δ9-tetrahydrocannabinol derivatives." Chemical and pharmaceutical bulletin 46.9 (1998): 1462-1467. DOI: 10.1248/cpb.46.1462.

* cited by examiner

*Primary Examiner* — Rei Tsang Shiao

(74) *Attorney, Agent, or Firm* — The Roy Gross Law Firm, LLC; Roy D. Gross

(57) ABSTRACT

Provided herein are THC derivatives, formulations thereof, synthesis thereof and uses thereof through oral administration, for treatment of diseases and disorders.

15 Claims, 18 Drawing Sheets

1

2

3

General retrosynthetic analysis

4 + acetoxy butadiene

5

6

7 olivetol

8

1

9-desmethyl THC

Synthesis of 9-$CD_3$-(8-$D_2$)-THC triethyl phosphonoacetate acetone-d6

9

10

11

12

4

13

14

15

16

17 olivetol

9-$CD_3$-(8-$D_2$)-THC acryloyl chloride oxazolidinone

4

15 olivetol

17

17

9-CD$_3$-(8-D$_2$) THC (3)

Synthesis of 9-$CF_3$ THC

Trifluoroacetic anhydride + Ethyl vinyl ether → 18

19 + 4 → 20 → 21 → 22

22 + Olivetol → 2 9-$CF_3$ THC

THC DERIVATIVES, ORAL DOSAGE FORMS COMPRISING SAME, USES THEREOF FOR TREATING DISEASES AND DISORDERS AND SYNTHESIS THEREOF

CROSS REFERENCE TO RELATED APPLICATIONS

This application is a Bypass Continuation of PCT Patent Application No. PCT/IL2021/051279 having International filing date of Oct. 28, 2021, which claims the benefit of priority of U.S. Provisional Patent Application No. 63/108,385, filed Nov. 1, 2020, the contents of which are all incorporated herein by reference in their entirety.

FIELD OF THE INVENTION

Provided herein are THC derivatives and uses thereof through oral administration, for treatment of diseases and disorders.

BACKGROUND

Cannabis is a genus of flowering plants that includes three putative species, *Cannabis sativa, Cannabis indica*, and *Cannabis ruderalis*. Cannabis and cannabis-based medicinal products have taken a huge step forward in the last decade, applied to many diseases. The main therapeutic and psychoactive component in cannabis flower is Δ-9-tetrahydrocannabinol, commonly known as tetrahydrocannabinol or THC (FIG. 1A).

THC can be isolated from marijuana (a mixture of leaves and flowering heads of the plant *Cannabis Sativa*). Alternatively, THC can be obtained by synthetic routes, e.g. as described in WO 02/096899 and U.S. Pat. No. 7,449,589. Enantiomerically pure THCs are required for formulation into drug products. THC exerts its activity by binding to specific receptors in the brain called cannabinoid receptors and, in doing so, causes some pain reduction, may reduce aggression, can stimulate appetite, and helps reduce nausea among other activities.

When administered orally, THC is oxidized in the liver mainly into the active metabolite 11-OH-THC, and then further into the inactive 9-nor-9-carboxy-THC (FIG. 1B). 11-OH-THC penetrates the blood brain barrier four times more quickly than THC itself, causing a markedly higher psychoactive effect. This higher psychoactive effect makes the oral use of THC a less desirable administration method, mainly for patients who suffer from chronic conditions that require cannabis treatment on a daily basis.

There is an unmet need for synthetic metabolically stable analogs of THC.

SUMMARY

There are provided metabolically stable THC derivatives that do not undergo oxidation resulting with 11-OH-THC and/or THC-COOH, or undergo slow oxidation.

Surprisingly, oral administration of the THC derivatives disclosed herein provides improved pharmacokinetics, longer duration of therapeutic activity and less side effects compared to oral administration of the parent molecule-THC. Accordingly, use of the THC derivatives disclosed herein provides the desired therapeutic effect at lower doses than required with THC, and moreover with lower side effects compared to THC, when administered orally.

Moreover, use of the of THC derivatives disclosed herein for oral administration improves the accessibility and adoption of cannabis treatment, particularly by older populations, which seem to prefer drug intake via oral consumption, e.g. in the form of tablets arranged in a weekly order, over smoking or inhalation.

Advantageously, the THC derivatives disclosed herein were obtained by relatively gentle modifications at position 11, which includes methyl in the original THC molecule (FIG. 1), thereby maintaining THC activity, via its interaction with cannabinoid receptors, similar to the activity of the parent THC, while preventing, or reducing, interactions with metabolic enzymes and thereby preventing the formation of the undesired metabolites 11-OH-THC, and the inactive 9-nor-9-carboxy-THC (FIG. 1B).

The THC derivatives disclosed herein have the structure of Formula I (FIG. 2A):

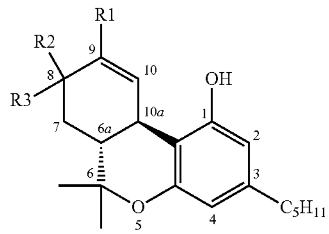

There is provided herein, according to some embodiments, a THC derivative having the structure of Formula I:

(I)

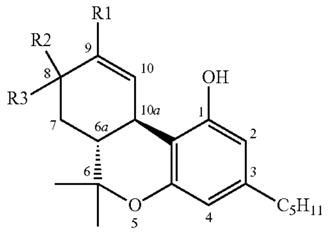

or enantiomer, acid, ester, a pharmaceutically acceptable salt, or prodrug thereof, wherein:

R1 is a substituted methyl group $CX_3$ wherein X is selected from a group consisting of deuterium and fluorine; and R2 and R3, independently, are selected from hydrogen and deuterium, wherein, when X is deuterium, each of R2 and R3 are also deuterium.

According to some embodiments, X may be fluorine.

According to some embodiments, X may be deuterium.

According to some embodiments, when X is fluorine, each of R2 and R3 are hydrogen atoms.

There is further provided herein, according to some embodiments, a pharmaceutical composition comprising one or more THC derivatives disclosed herein.

There is provided herein, according to some embodiments, a pharmaceutical composition comprising a THC derivative having the structure of Formula II (described in FIG. 2B).

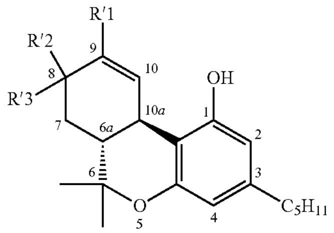

(II)

or enantiomer, acid, ester, or a pharmaceutically acceptable salt, or prodrug thereof, wherein R'1 is selected from a hydrogen and a substituted methyl group $CX_3$ where X is fluorine or deuterium; R'2 is hydrogen or deuterium; and R'3 is hydrogen or deuterium.

According to some embodiments, each of R'1, R'2 and R'3 is a hydrogen.

According to some embodiments, R'1 is a substituted methyl group $CX_3$ where X is fluorine.

According to some embodiments, R'1 is a substituted methyl group $CX_3$ where X is deuterium and each of R'2 and R'3 is a hydrogen.

According to some embodiments, R'1 is a substituted methyl group $CX_3$ where X is deuterium and each of R'2 and R'3 is deuterium.

According to some embodiments, the pharmaceutical composition in a dosage oral form.

According to some embodiments, the pharmaceutical composition in a liquid dosage form.

According to some embodiments, the pharmaceutical composition is for parenteral or enteral use.

According to some embodiments, the pharmaceutical composition is for treatment or prevention of a disease or disorder. The disease or disorder may be selected from pain, neurodegenerative diseases or disorders and insomnia. Each possibility is a separate embodiment.

There is further provided herein, according to some embodiments, a method of treating or preventing a disease or disorder, the method comprising administering to a subject in need thereof a pharmaceutical composition comprising one or more of the THC derivatives and/or the pharmaceutical compositions disclosed herein. Administering may include administering via a route of administration selected from the group consisting of oral administration, parenteral administration, enteral administration, and intravenous administration. Each possibility is a separate embodiment.

There is further provided herein, according to some embodiments, a process of synthesizing 9-$CD_3$-(8-$D_2$)-THC (shown in FIG. 8 and FIG. 9), the process comprises the steps of:

coupling (1R,6R)-6-(1-Hydroxy-1-methylethyl)-cyclohex-2-en-1-[(1,1-dimethylethyl)dimethylsilyloxy)]-4-(methyl-$d_3$)-5-$d_2$ (compound 15) with olivetol to provide 1,3-Dihydroxy-2-((1R,6R)-6-(1-Hydroxy-1-methylethyl)-4-(methyl-$d_3$)-5-$d_2$-cyclohex-2-en-1-yl)-5-pentylbenzene (compound 17); and cyclization of compound 17 to provide 9-$CD_3$-(8-$D_2$)-THC.

According to some embodiments, compound 15 (shown in FIG. 6) may be produced according to a process which includes one or more of the steps of:

Horner-Wadsworth-Emmons reaction between triethyl phosphoacetate and acetone-do in the presence of sodium hydride to produce 3-(methyl-$d_3$)-2-Butenoic acid-ethyl ester (compound 9)

reduction 4,4,4-$d_3$, 3-(methyl-$d_3$)-2-Butenoic acid-ethyl ester (compound 9) to the corresponding alcohol-4,4,4-$d_3$, 3-(methyl-$d_3$)-2-Buten-1-ol (compound 10);

mild oxidation of compound 10 to give 4,4,4-$d_3$, 3-(methyl-$d_3$)-2-Butenal (compound 11);

reacting compound 11 with t-butyldimethylchloro silane under basic conditions to produce (1,1-dimethylethyl) dimethyl[(4,4-$d_2$, 3-(methyl-$d_3$)-1,3-butadien-1-yl) oxy]-Silane (compound 12);

reacting compound 4 with compound 12 in the presence of a chiral catalyst to produce 3-[(1R,2R)-2-((1,1-dimethylethyl)dimethylsilyloxy)-4-(methyl-$d_3$)-5-$d_2$-cyclohex-3-en-1-ylcarbonyl]-2-oxazolidinone (compound 13);

transesterification of compound 13 to produce Benzyl-(1R,2R)-2-(1,1-dimethylethyl)dimethylsilyloxy)-4-(methyl-$d_3$)-5-$d_2$-cyclohex-3-en-1-carboxylate (compound 14); and Grignard reaction of compound 14 to produce compound 15.

Other objects, features and advantages of the present invention will become clear from the following description, examples, and drawings.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. For the sake of clarity, some objects depicted in the figures are not to scale.

In the Figures.

DETAILED DESCRIPTION

Figure 1A:
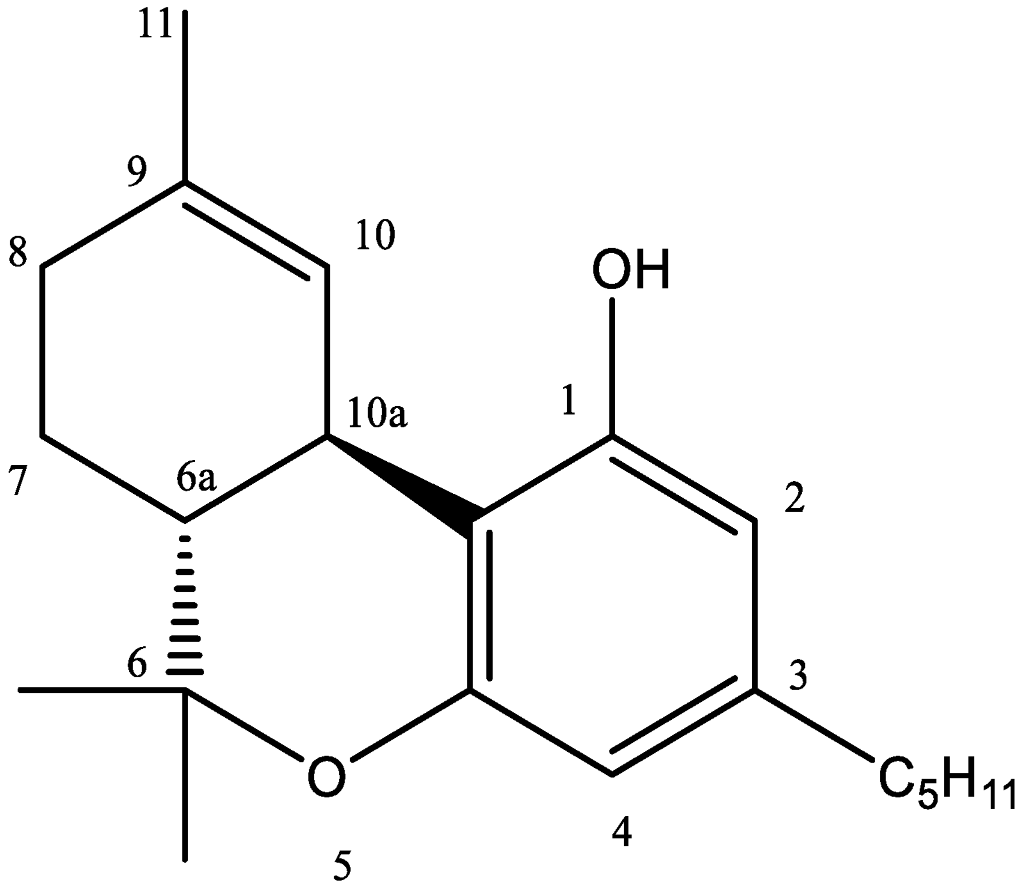
FIG. 1A represents THC.

The principles, uses and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout. In the figures, same reference numerals refer to same parts throughout.

In the description and claims of the application, the words "include" and "have", and forms thereof, are not limited to members in a list with which the words may be associated.

Figure 1B:
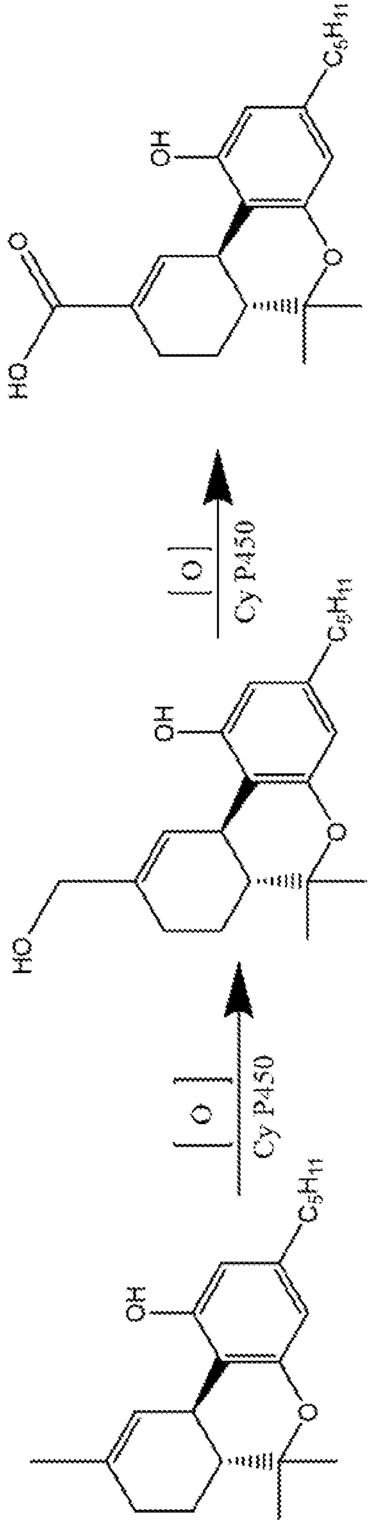
FIG. 1B represents, from left to right, THC and THC metabolites 11-OH-THC and 11-nor-9-carboxy-THC (THC-COOH).
Figure 2A:
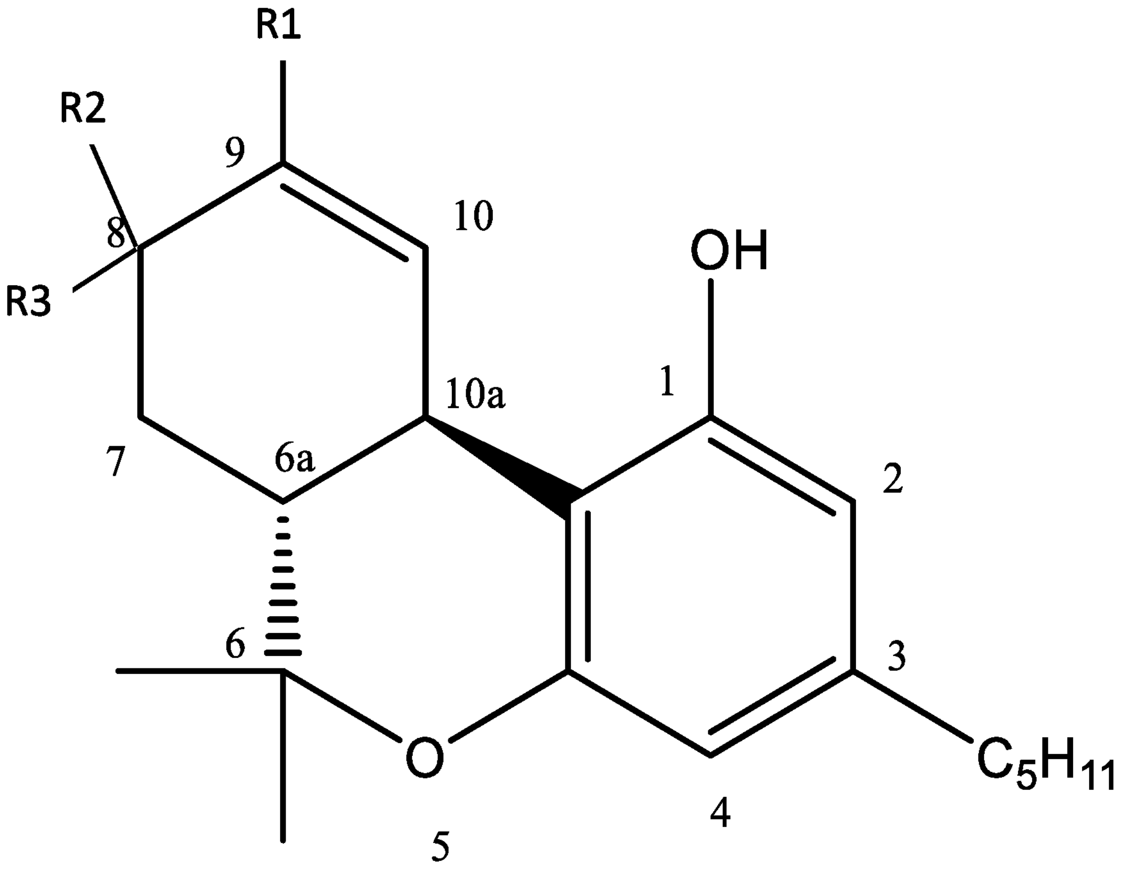
FIG. 2A represents THC derivative of Formula I, according to some embodiments.
Figure 2B:
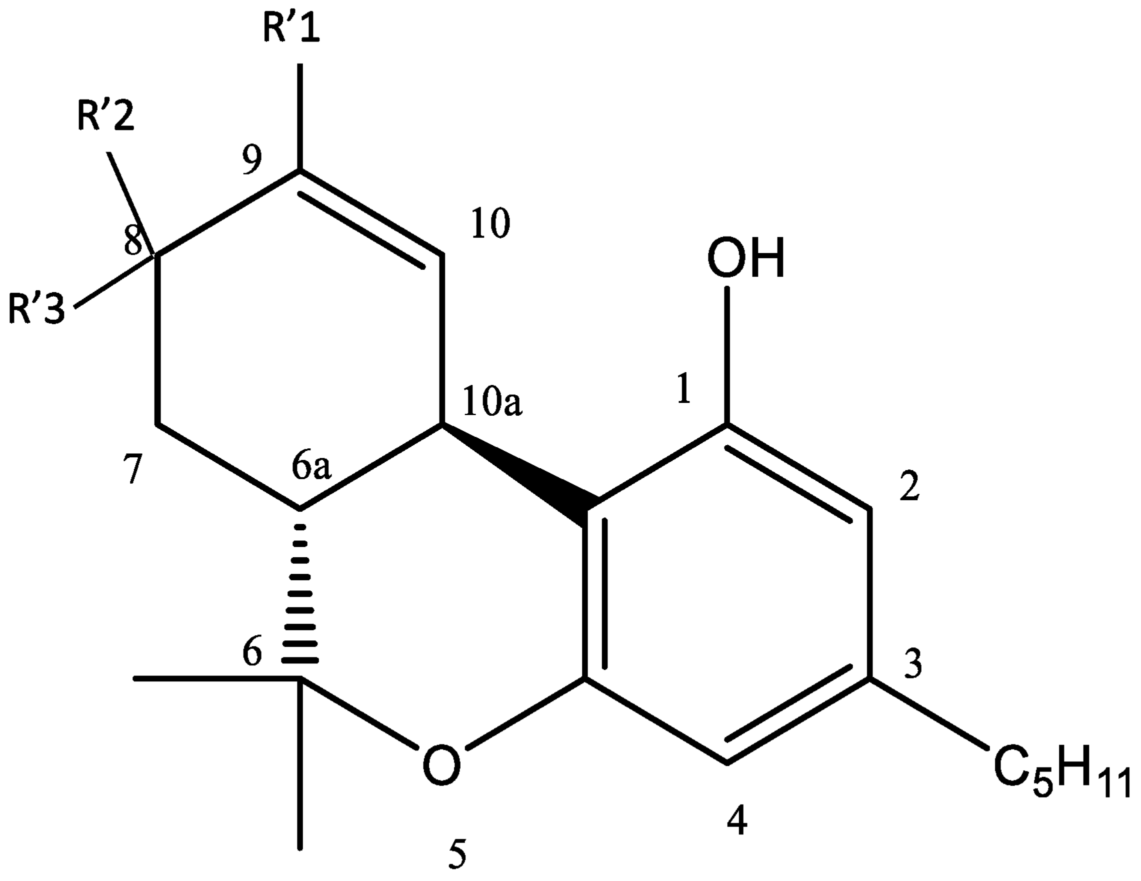
FIG. 2B represents THC derivative of Formula II, according to some embodiments.

Cannabinoid (CB) possess numerous therapeutic properties including analgesia, ocular hypotension, and antiemesis. CBs-based medications are currently applied for treatments of a wide range of medical conditions, such as, neuropathic pain, pain related to cancer and trauma, spasticity associated with multiple sclerosis and fibromyalgia. THC (FIG. 1A), a component of CB, is metabolized mainly to 11-Hydroxy THC (FIG. 1B) in the stomach when administered orally. This metabolite is even more psychoactive than the parent THC, and leads to undesired side effects. It is further oxidized to 11-nor-9-carboxy THC (THC acid; FIG. 1B), which is not active.

However, oral administration of cannabis, or its active components, is considered preferable and safer over smoking or inhalation, in particular for first-time users, non-smokers, children and the elderly population. In addition, smoking is associated with lung diseases, and particularly, with lung cancer risks.

The THC derivatives and the pharmaceutical compositions disclosed herein address the need for THC analogues for oral administration, having improved pharmacokinetics and reduced side effects, primarily side effect induced by undesired metabolites.

Provided herein, according to some embodiments, THC derivative having the structure of Formula I:

(I)

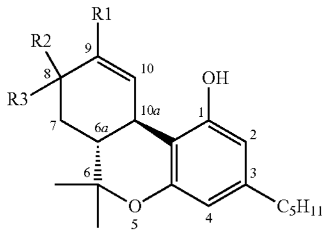

or enantiomer, acid, ester, a pharmaceutically acceptable salt, or prodrug thereof, wherein: R1 is a substituted methyl group $CX_3$ wherein X is selected from a group consisting of deuterium and fluorine; and R2 and R3, independently, are selected from hydrogen and deuterium, wherein, when X is deuterium, each of R2 and R3 are also deuterium.

The term "derivative" as used herein refers to synthetic derivatives and is exchangeable with term 'analogues' or 'analogs'. An analog herein refers to a compound that is derived from a naturally occurring THC by chemical or synthetic transformation of the naturally occurring THC or a synthetic or a partially synthetically derived substance that is similar or near similar to a THC in question.

The THC derivatives disclosed herein contain one or more asymmetric center (also referred to as a chiral center) and may, therefore, exist as individual enantiomers, diastereomers, or other stereoisomeric forms, or as mixtures thereof, collectively termed herein 'enantiomers'. Chiral centers, such as chiral carbon atoms, may also be present in a substituent such as an alkyl group. Where the stereochemistry of a chiral center present in the THC derivative is not specified, the structure is intended to encompass any stereoisomer and all mixtures thereof. Thus, the THC derivative disclosed herein may be used as racemic mixtures, enantiomerically enriched mixtures, or as enantiomerically pure individual stereoisomer.

In some embodiments, R1 is a substituted methyl group $CX_3$ where X is fluorine. In some embodiments, $CX_3$ is $CF_3$ and each of R2 and R3, is a hydrogen.

In some embodiments, the THC derivative comprises 9-$CF_3$-THC. In some embodiments, the THC derivative is consisting of 9-$CF_3$-THC. In some embodiments, the THC derivative is 9-$CF_3$-THC having the following structure:

2

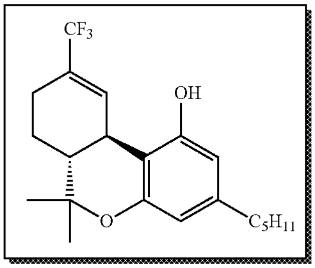

In some embodiments, R1 is a substituted methyl group $CX_3$ where X is deuterium, and each of R2 and R3 is deuterium.

Figure 3A:
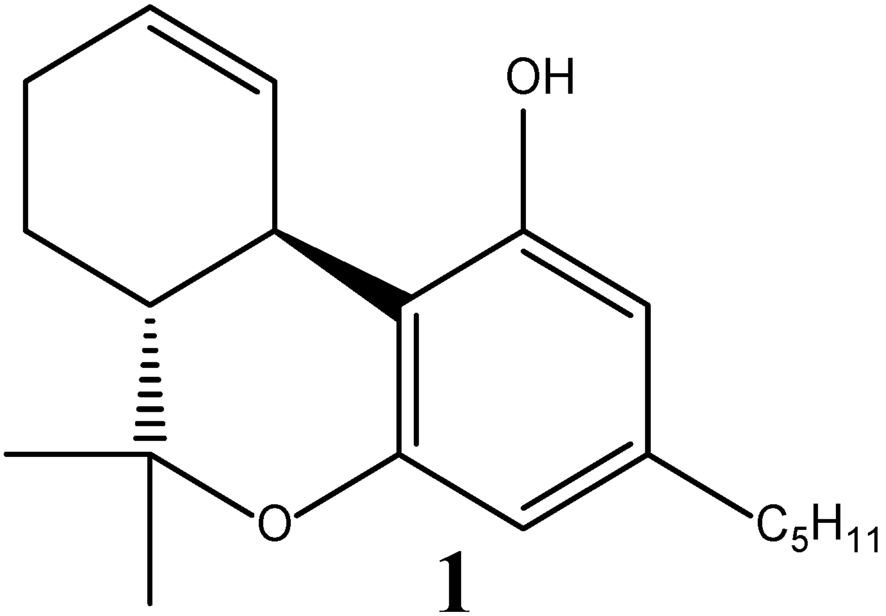
FIG. 3A represents the THC derivative 9-desmethyl-THC, according to some embodiments.
Figure 3B:
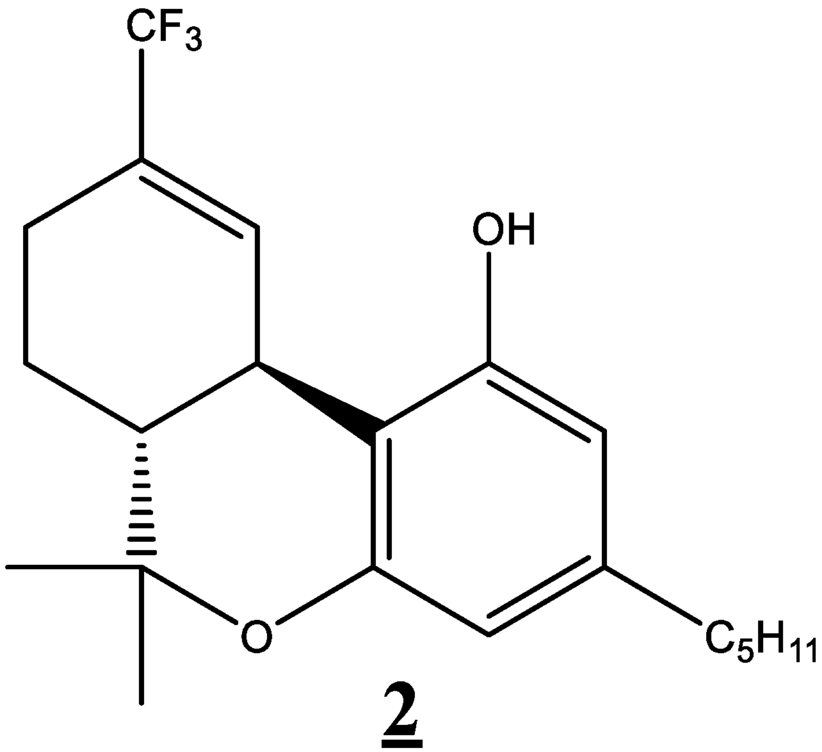
FIG. 3B represents the THC derivative 9-trifluoromethyl-THC, according to some embodiments.
Figure 3C:
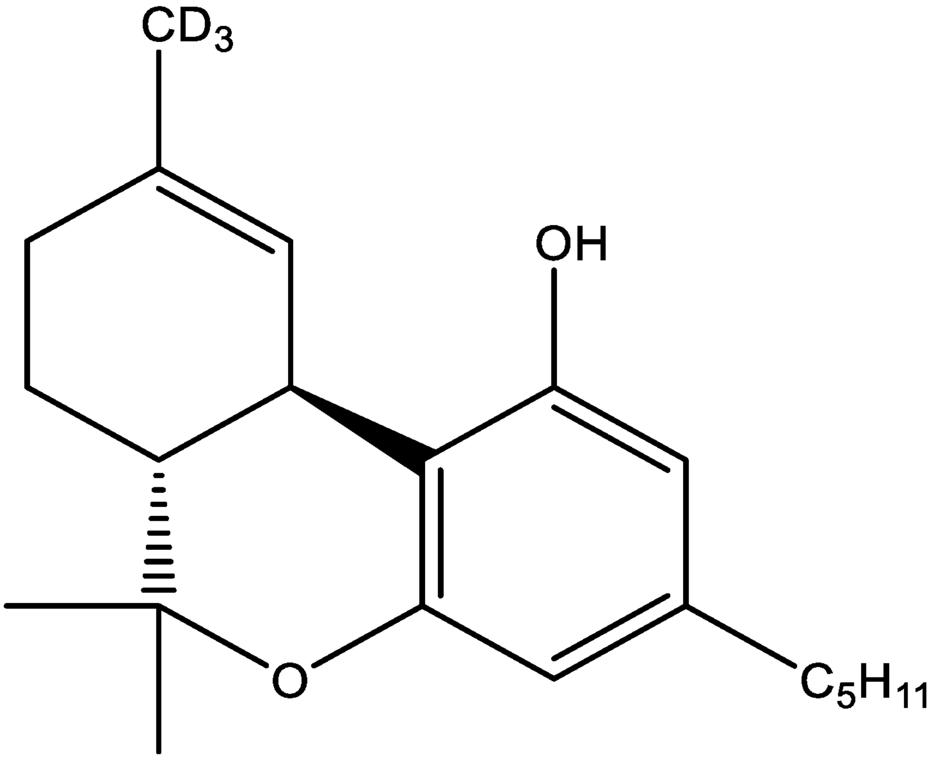
FIG. 3C represents the THC derivative 9-$CD_3$-THC, according to some embodiments.
Figure 3D:
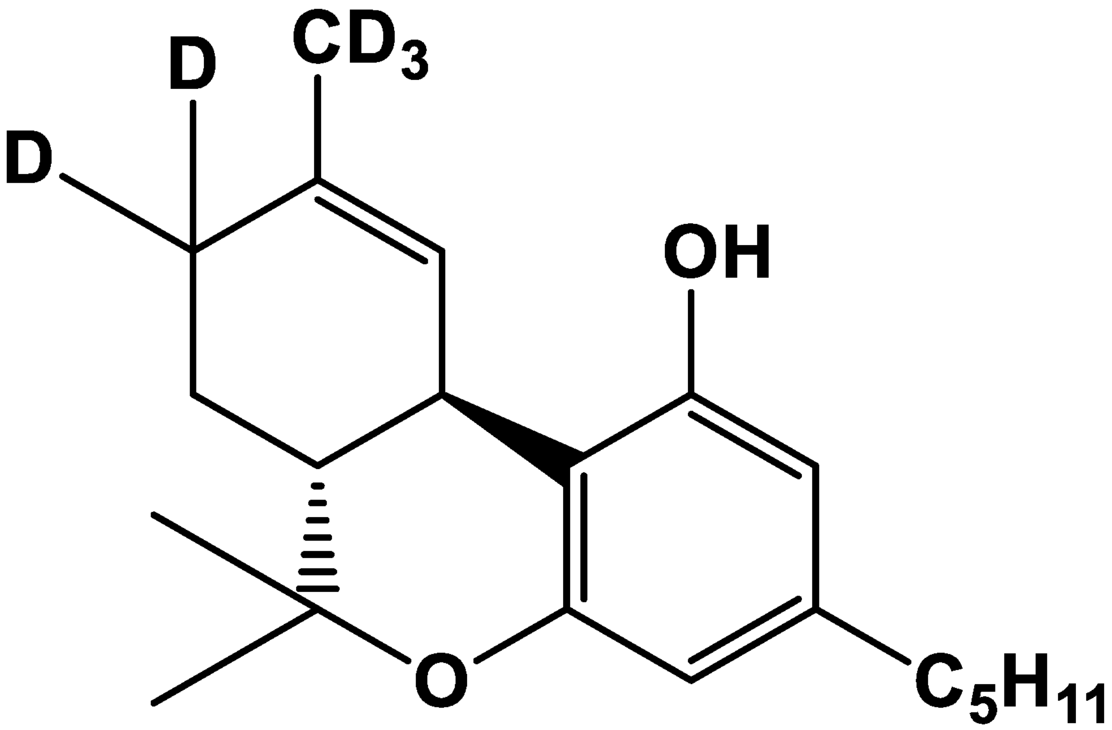
FIG. 3D represents the THC derivative 9-$CD_3$-(8-$D_2$)-THC, according to some embodiments.

In some embodiments, the THC derivative comprises 9-$CD_3$-(8-$D_2$)-THC (shown in FIG. 3D). In some embodiments, the THC derivative is consisting of 9-$CD_3$-(8-$D_2$)-

THC. In some embodiments, the THC derivative is 9-$CD_3$-(8-$D_2$)-THC having the following structure:

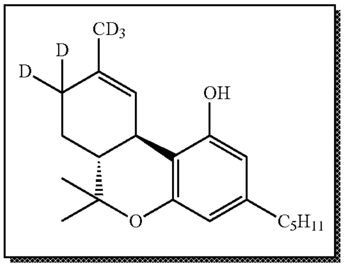

As exemplified below, the THC derivatives disclosed herein exhibit improved metabolic stability compared to the parent molecule THC. Thus, the THC derivatives disclosed herein exhibit advantageous pharmacokinetics compared to THC, specifically, via oral administration.

In some embodiments, there is provided a pharmaceutical composition comprising the THC derivatives of Formula I. In some embodiments, the pharmaceutical composition comprises 9-$CF_3$-THC. In some embodiments, the pharmaceutical composition comprises 9-$CD_3$-(8-$D_2$)-THC.

Pharmaceutical Compositions

Provided herein are pharmaceutical compositions, the pharmaceutical composition comprising a THC derivative having the structure of Formula II:

(II)

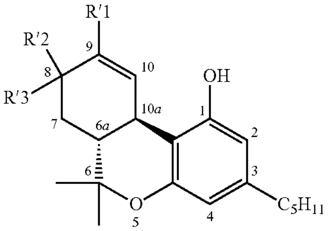

or enantiomer, acid, ester, or a pharmaceutically acceptable salt, or prodrug thereof, wherein R'1 is selected from a hydrogen and a substituted methyl group $CX_3$ where X is fluorine or deuterium; R'2 is hydrogen or deuterium; and R'3 is hydrogen or deuterium; and pharmaceutically acceptable excipients.

In some embodiments, each of R'1, R'2 and R'3 is a hydrogen.

In some embodiments, R'1 is a substituted methyl group $CX_3$ where X is fluorine.

In some embodiments, R'1 is a substituted methyl group $CX_3$ where X is deuterium. In some embodiments, X is deuterium and each one of R'2 and R'3 is hydrogen. In some embodiments, X is deuterium and one of R'2 and R'3 is deuterium and the other one is hydrogen. In some embodiments, each of X, R'2 and R'3 is deuterium.

In some embodiments, the pharmaceutical composition comprising a THC derivative selected from: 9-$CF_3$-THC; 9-$CD_3$-(8-$D_2$)-THC; 9-desmethyl-THC and 9-$CD_3$-THC. Each possibility is a separate embodiment of the present invention.

In some embodiments, the pharmaceutical composition comprises 9-$CF_3$-THC. In some embodiments, the pharmaceutical composition comprises 9-$CD_3$-(8-$D_2$)-THC.

In some embodiments, the pharmaceutical composition comprises 9-desmethyl-THC having the following structure:

1

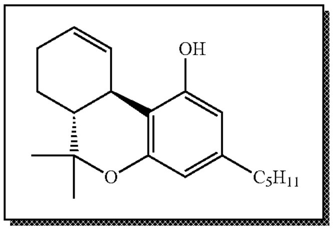

In some embodiments, the pharmaceutical composition comprises 9-$CD_3$-THC having the following structure:

3

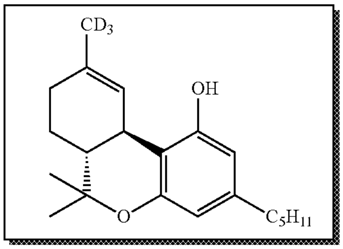

It is noted that the pharmaceutical compositions disclosed herein provide beneficial pharmacokinetics and excess metabolic stability, via oral administration, compared to THC.

A typical pharmaceutical composition, also known as formulation, is prepared by mixing the THC derivative discloses herein and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., the THC derivative or a pharmaceutical composition comprising same) or aid in the manufacturing of the pharmaceutical product (i.e., medicament).

The formulations may be prepared using conventional dissolution and mixing procedures. For example, the bulk drug substance (i.e., the THC derivative) is dissolved in a suitable solvent in the presence of one or more of the excipients described above. The THC derivative is typically formulated into pharmaceutical dosage forms to provide an easily controllable dosage thereof to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

In some embodiments, the pharmaceutical composition is for oral administration. In some embodiments, the pharmaceutical composition is in a dosage form for oral administration. In some embodiments, the dosage form includes, but is not limited to, a dosage form for sublingual or buccal mucosae administration. In some embodiments, the dosage form is an oral solid dosage form, such as gels, capsules, soft gel capsules, tablets, pastilles and lozenges.

Solid dosage forms suitable for oral administration include, but are not limited to, capsules, tablets, pills, powders, and granules. In such solid dosage forms, the THC derivative may be the only active ingredient or may be in combination with one or more active ingredients which are optionally mixed with at least one pharmaceutically acceptable excipient or carrier such as sodium citrate or dicalcium phosphate, and/or fillers or extenders such as starches, lactose, sucrose, glucose, mannitol, and silicic acid; binders such as, for example, carboxymethylcellulose, alginates, gelatin, polyvinylpyrrolidone, sucrose, and acacia; humectants such as glycerol; disintegrating agents such as agar-agar, calcium carbonate, potato or tapioca starch, alginic acid, certain silicates, and sodium carbonate; solution retarding agents such as paraffin; absorption accelerators such as quaternary ammonium compounds; wetting agents such as, for example, acetyl alcohol and glycerol monostearate; absorbents such as kaolin and bentonite clay; and lubricants such as talc, calcium stearate, magnesium stearate, solid polyethylene glycols, sodium lauryl sulfate, and mixtures thereof. For capsules, tablets and pills, in one embodiment, the dosage form can also comprise buffering agents.

In some embodiments, solid dosages in the form of tablets, capsules, pills, and granules may be coated using compounds that accelerate or decrease the release of the THC derivative. For instance, the solid dosages may have enteric coatings, extended-release coatings, sustained-release coatings, delayed release coatings and immediate-release coatings. Methods for coating solid dosage forms as well as the materials used to manufacture such coatings are well known in the art. The solid dosage forms may, optionally, contain opacity enhancing agents. According to an embodiment, the solid dosage form comprises an enteric coating that permits the release of the THC derivative alone or in combination with one or more active agents at a specific location within the gastrointestinal tract, optionally, in a delayed manner. Exemplary of such coating materials include glyceryl monostearate or glyceryl distearate, polymeric substances and waxes. The THC derivative, for instance, can be provided alone or in combination with one or more drugs that can also be in micro-encapsulated form, if appropriate, with one or more of the above-mentioned excipients.

In some embodiments, the dosage form is a soft-gelatin capsule comprising type A and/or B gelatin, water, a plasticizer, such as glycerin or sorbitol; and encapsulates a compound containing a liquid mixture that includes: the THC derivative, an oil (e.g. sesame oil), methyl and propyl parabens.

In some embodiments, the pharmaceutical composition is in the form of micelles or liposomes that encapsulate the THC derivative within the membrane of the micelles or liposomes. Within the context of the present technology, the term "micelle" refers to an aggregate of surfactant molecules dispersed in a liquid colloid, while "liposome" refers to a vesicle composed of a mono or bilayer lipid.

In some embodiments, the surfactant is selected from the group of: cremophor, RH 40, Labrasol, Tween 20 and Tween 80. In some embodiments, the surfactant comprises cremophor. Cremophore is a synthetic, nonionic surfactant commonly used for stabilizing emulsions of nonpolar materials in water.

In yet another embodiment, other drugs and pharmaceutically acceptable carriers, if present, may be in the lipophilic membrane or entrapped in the aqueous fluid that forms the core of the liposome. The entrapped THC derivative may contribute to the stability of the micelle/liposome membranes, such that the micelle/liposomes formulations may be used as an improved, fast, reliable and efficient system for the oral delivery of the THC derivative and/or the additional drugs to subjects in need thereof.

In some embodiments, the pharmaceutical composition is for parenteral administration. In some embodiments, the pharmaceutical composition is in a dosage form for parenteral administration. In some embodiments, the parenteral administration includes, but is not limited to, subcutaneous, intramuscular, intravenous, intraarterial, intradermal, intrathecal and epidural.

Where the compound is administered parenterally, it may be formulated with a pharmaceutically acceptable parenteral vehicle and in a unit dosage injectable form.

In some embodiments, the pharmaceutical composition is for enteral administration. In some embodiments, the enteral administration includes, but is not limited to, administration to the esophagus, stomach, and small and large intestines (i.e., the gastrointestinal tract). Methods of enteral administration include oral, sublingual (dissolving the drug under the tongue) and rectal.

Other routes of administration may be suitable, including, but not limited to, transdermal, rectal, nasal, topical (including buccal and sublingual), vaginal, intraperitoneal, intrapulmonary and intranasal. For local pain treatment, the THC derivatives may be administered topically. It will be appreciated that the preferred route of administration may vary with, for example, the condition of the recipient.

The amount of THC derivative in each dosage form can be determined by titration of doses which are beneficial to patients as they can take smaller doses of the medication to achieve efficacy. Clearly, not all patients require the same dose of medication; for example, a patient with fast metabolism may require a higher dose than a patient of slower metabolism. In some embodiments, said titration is adjusted with a time-release and point of release-tailored dosage forms, for example, a gelatin capsule or a tablet designed to release medication in doses in certain parts of the digestive system to achieve the desired efficacy.

A "unit dosage" or a "dosage form" refer to a maximum dose of medication that can be taken per single administration or per treatment regimen. Depending on the administration route a dosage may fluctuate significantly, such that unit dosage may consist of multiple doses taken several times a day.

The term “subject” is interchangeable with “patient” and refers to a mammal in need of treatment or undergoing treatment using the inventive THC derivatives described herein. Mammalian subjects include without limitation humans or any other animal in need of treatment.

Effective amounts of the THC derivatives disclosed herein may be determined empirically. Upon administering to a subject, the total daily usage of the THC derivatives will be decided by the attending physician within the scope of sound medical judgment. The specific therapeutically effective dose level for any patient will depend upon a variety of factors: the type and degree of the response to be achieved; the activity of the specific compound employed; the age, body weight, general health, sex and diet of the patient; the duration of the treatment; drugs used in combination or coincidental with the method of the invention; and like factors well known in the medical arts.

Treatment

The pharmaceutical compositions disclosed herein are suitable for the treatment or prevention of various diseases and disorders, including, but not limited to, autoimmune diseases and disorders, motor neuron diseases and disorders, neurodegenerative diseases and disorders, pain associated with cancer and trauma, anti-convulsant and anti-psychotics drugs-related symptoms, metabolic and endocrine-related diseases and disorders; athetosis-related to damage or degeneration of basal ganglia, minor tranquilizers and alcohol withdrawal syndromes, symptoms or side effects associated with anti-retroviral therapy, chemotherapy and radiation therapy. Each possibility is a separate embodiment of the present invention.

Thus, in some embodiments, there is provided a method for treating a disease or disorder, the method comprising administering to a subject in need thereof a pharmaceutical composition comprising at least one of the THC derivatives disclosed herein.

In some embodiments, the THC derivative is a THC derivative of Formula I. In some embodiments, the THC derivative is the THC derivative of Formula II. In some embodiments, the THC derivative is selected from the group consisting of: 9-desmethyl-THC, 9-trifluoromethyl-THC, 9-$CD_3$-THC and 9-$CD_3$-(8-$D_2$)-THC.

In some embodiments, said treating the disease or disorder comprises preventing the disease or disorder, ameliorating the severity and/or symptoms of the disease or disorder, ameliorating clinical manifestation of the disease or disorder, reducing the number and/or reducing frequency of symptoms. Each possibility is a separate embodiment of the present invention.

In some embodiments, said administering comprises oral administration. In some embodiments, said administering is oral administration.

In some embodiments, said administering comprises parenteral administration. In some embodiments, the parenteral administration comprise any one or more of intravenous administration, topical administration, transdermal administration and intramuscular administration. Each possibility is a separate embodiment of the present invention.

In some embodiments, said administering comprises enteral administration. In some embodiments, the enteral administration comprises any one or more of oral, sublingual and rectal administration. Each possibility is a separate embodiment of the present invention.

In some embodiments, there is provided a pharmaceutical composition comprising at least one of the THC derivatives disclosed herein for the treatment of a disease or disorder.

In some embodiments, the pharmaceutical composition is in an oral dosage form. In some embodiments, the pharmaceutical composition is in a dosage form for parenteral administration. In some embodiments, the pharmaceutical composition is in a dosage form for enteral administration.

In some embodiments, there is provided a pharmaceutical composition comprising at least one of the THC derivatives disclosed herein for use in the treatment of a disease or disorder.

In some embodiments, there is provided use of a pharmaceutical composition comprising at least one of the THC derivatives disclosed herein for the treatment of a disease or disorder.

In some embodiments, the disease or disorder is selected from: pain, cancer related pain, neurodegenerative diseases or disorders, Alzheimer’s Disease, multiple sclerosis (MS), ALS, Parkinson’s, fibromyalgia, insomnia, anxiety and constipation. Each possibility is a separate embodiment of the present invention.

In some embodiments, the disease or disorder is pain. In some embodiments, the disease or disorder is a chronic pain.

In some embodiments, the pharmaceutical composition comprising at least one of the THC derivatives further includes at least one additional active agent. In some embodiments, the pharmaceutical composition comprising at least one of the THC derivatives is for use in combination with at least one additional active agent. In some embodiments, the pharmaceutical composition comprising at least one of the THC derivatives is administered in combination with at least one additional active agent.

In some embodiments, the at least one additional active agent is chemotherapy, such as, cyclophosphamide, doxorubicin and cisplatin. In some embodiments, the at least one additional active agent is an anti-inflammatory agent, including non-steroidal anti-inflammatory agent, such as, ibuprofen, aspirin and naproxen. In some embodiments, the at least one additional active agent comprises antibiotics, such as, penicillin and tetracycline. In some embodiments, the at least one additional active agent comprises an analgesic agent, such as, morphine. In some embodiments, the at least one additional active agent is a pain killer. In some embodiments, the at least one additional active agent is an anti-convulsant agent. In some embodiments, the at least one additional active agent comprises hormonal therapy. In some embodiments, the at least one additional active agent comprises an antidepressant, such as, selective serotonin reuptake inhibitors, Serotonin-norepinephrine reuptake inhibitors and tricyclic antidepressants. In some embodiments, the at least one additional active agent comprises an antipsychotic medication. In some embodiments, the at least one additional active agent comprises a tranquilizer. In some embodiments, the at least one additional active agent is an anxiolytic medication, such as, benzodiazepines and antihistamine.

In some embodiments, one or more of the THC derivatives disclosed herein may be used as or in food/beverage products.

In some embodiments, the pharmaceutical compositions disclosed herein are use, or administered, in combination with medical procedures, such as, surgery and radiotherapy.

Synthesis:

In some embodiments, there is provided a process of synthesizing 9-desmethyul THC.

In some embodiments, there is provided a process of synthesizing 9-$CF_3$-THC.

In some embodiments, there is provided a process of synthesizing 9-$CD_3$-(8-$D_2$)-THC.

In some embodiments, there is provided a process of synthesizing 9-$CD_3$ THC.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

EXAMPLES

Example 1: General Strategy for Synthesizing THC Derivatives

Figure 4A:
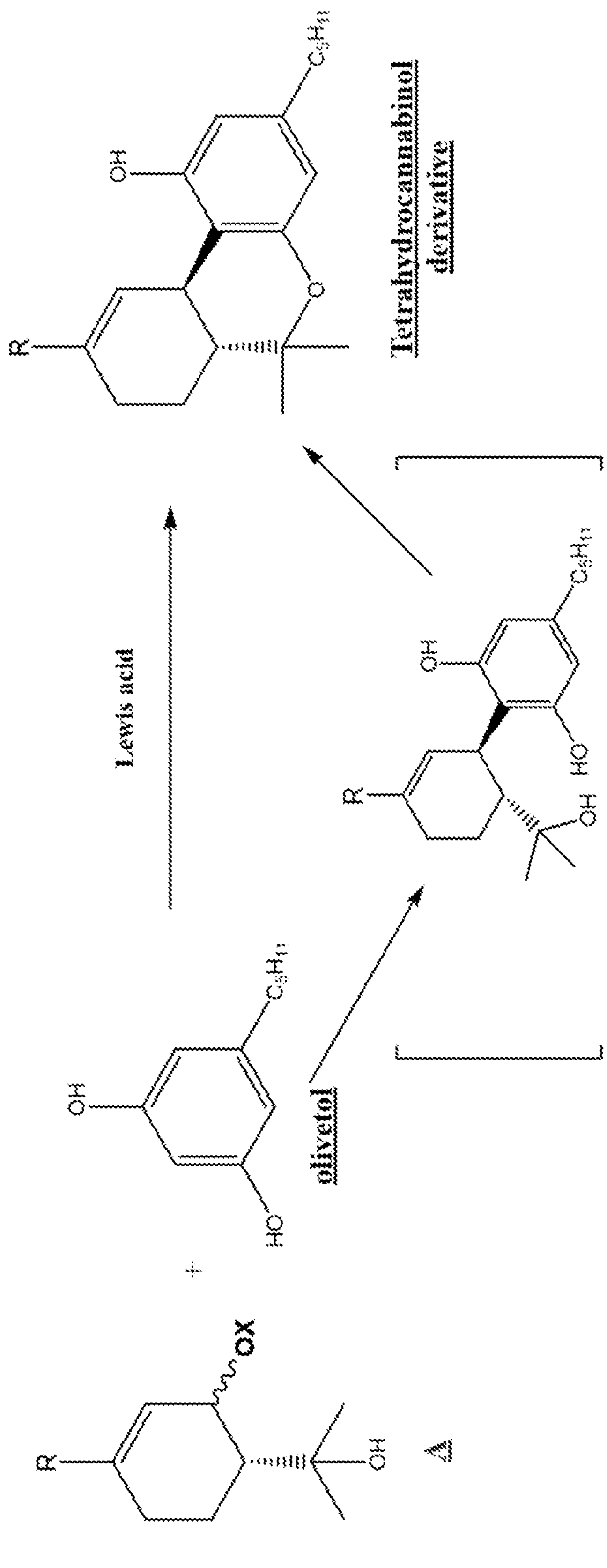
FIG. 4A represents the outlines of the process for the preparation of the THC analogs disclosed herein, according to some embodiments.

The process for the preparation of the THC analogs disclosed herein is presented in FIG. 4A. As shown in FIG. 4A, in order to build the core of the desired THC derivatives, a terpene-based moiety (compound A) was coupled to olivetol (in the presence of a Lewis acid), followed by cyclization to the final desired material.

In order to introduce some other functionalities instead of the 9-methyl group, the structure of the starting materials leading to compound A was designed for each derivative such that it already bears the required modification of the 9-methyl group.

Figure 4B:
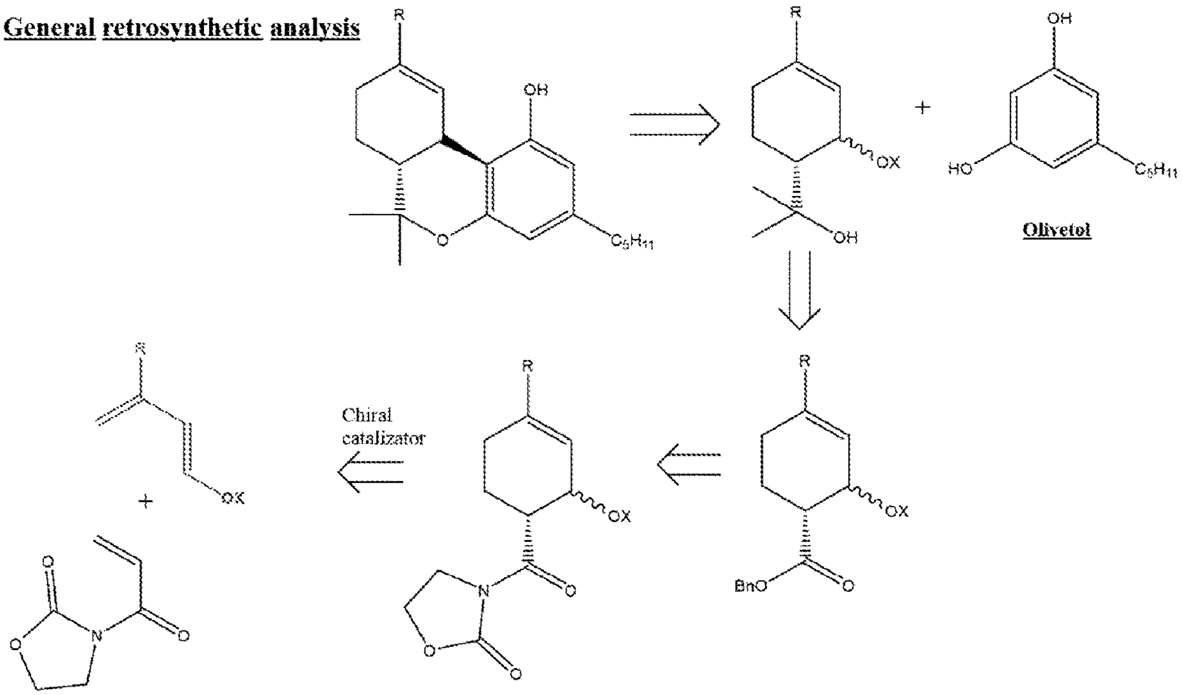
FIG. 4B represents a retrosynthetic analysis of the THC analogs disclosed herein, according to some embodiments.

The general retrosynthetic analysis for all the synthetic analog molecules of THC disclosed herein is presented in FIG. 4B.

Example 2: Synthesis of 9-Desmethyul THC

Figure 5:
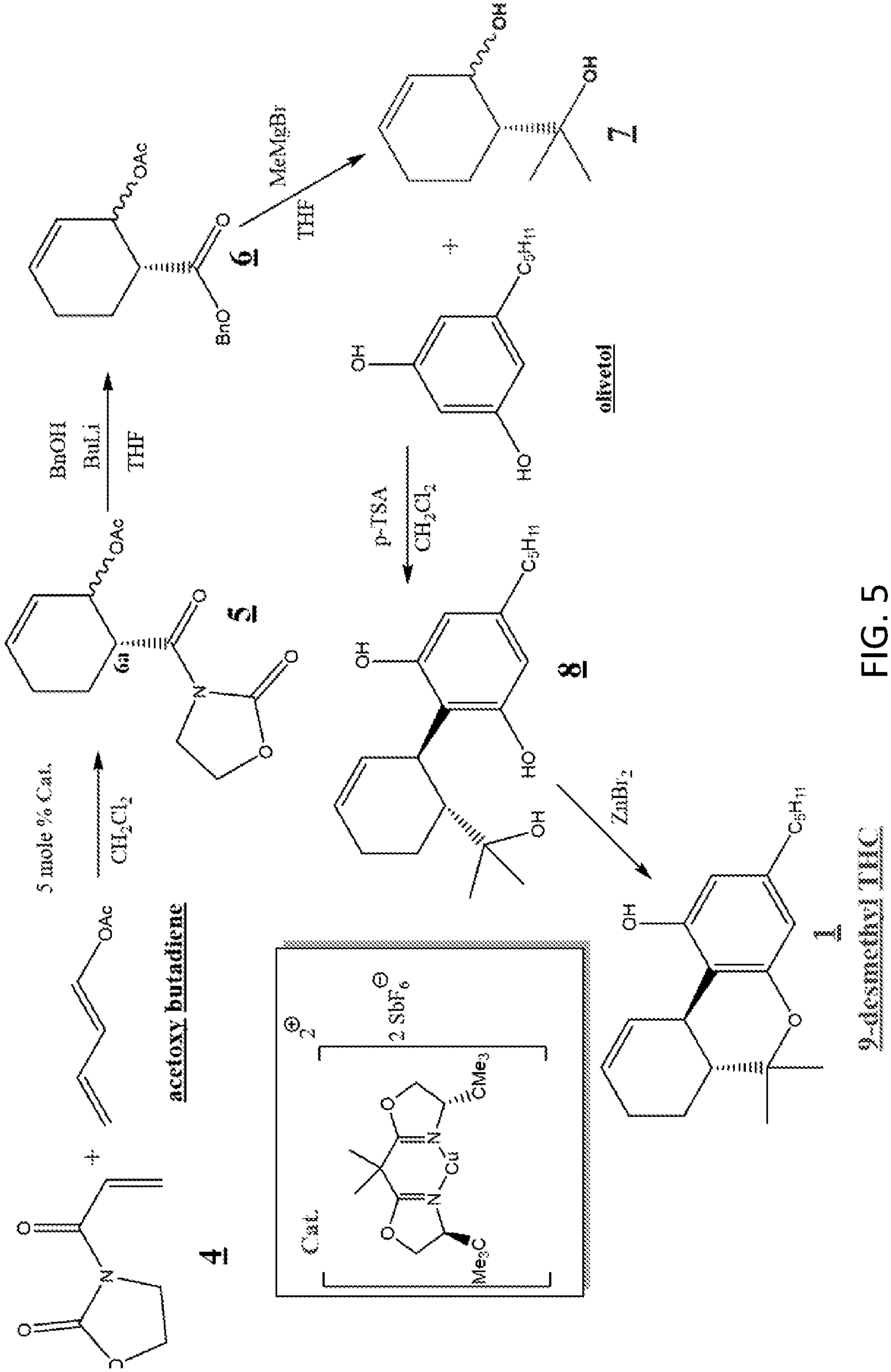
FIG. 5 represents the synthesis of 9-desmethyl THC, according to some embodiments.

Compound 7 (a variation of compound A which lacks the methyl group), was prepared as the key intermediate to be coupled with olivetol, towards the final material. The process is described in FIG. 5.

Based on Evans, D. A. et al., (J. Am. Chem. Soc. 1999, 121, 7582-7594), compound 4 and acetoxy butadiene in the presence of a chiral catalyst, [Cu((R,R)-t-Bu-box)]·$(SbF_6)_2$ was applied in the Diels-alder reaction towards compound 5, in order to obtain the correct stereochemistry at position 6a. Compound 5 underwent transesterification to give compound 6, which after Grignard reaction, gave compound 7. Compound 7, which is an analog molecule of compound A, was coupled with olivetol towards compound 8 followed by cyclization towards the final compound, 9-desmethyl THC (designated 1 in FIG. 5).

The advantage of 9-Desmethyl THC is that it lacks the key 11-Me group, and therefore cannot undergo the oxidation process resulting with the undesired compounds 11-Hydroxy THC and 11-nor-9-carboxy THC (THC acid).

5

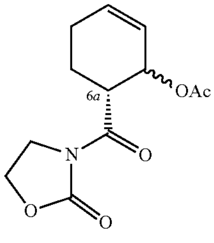

-continued

6

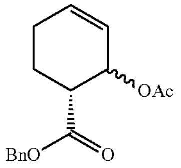

7

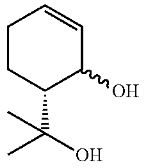

8

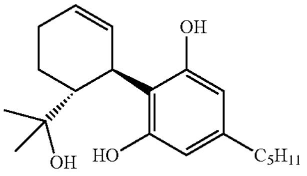

Example 3: Synthesis of 9-CD3-(8-D2) THC

Figure 6:
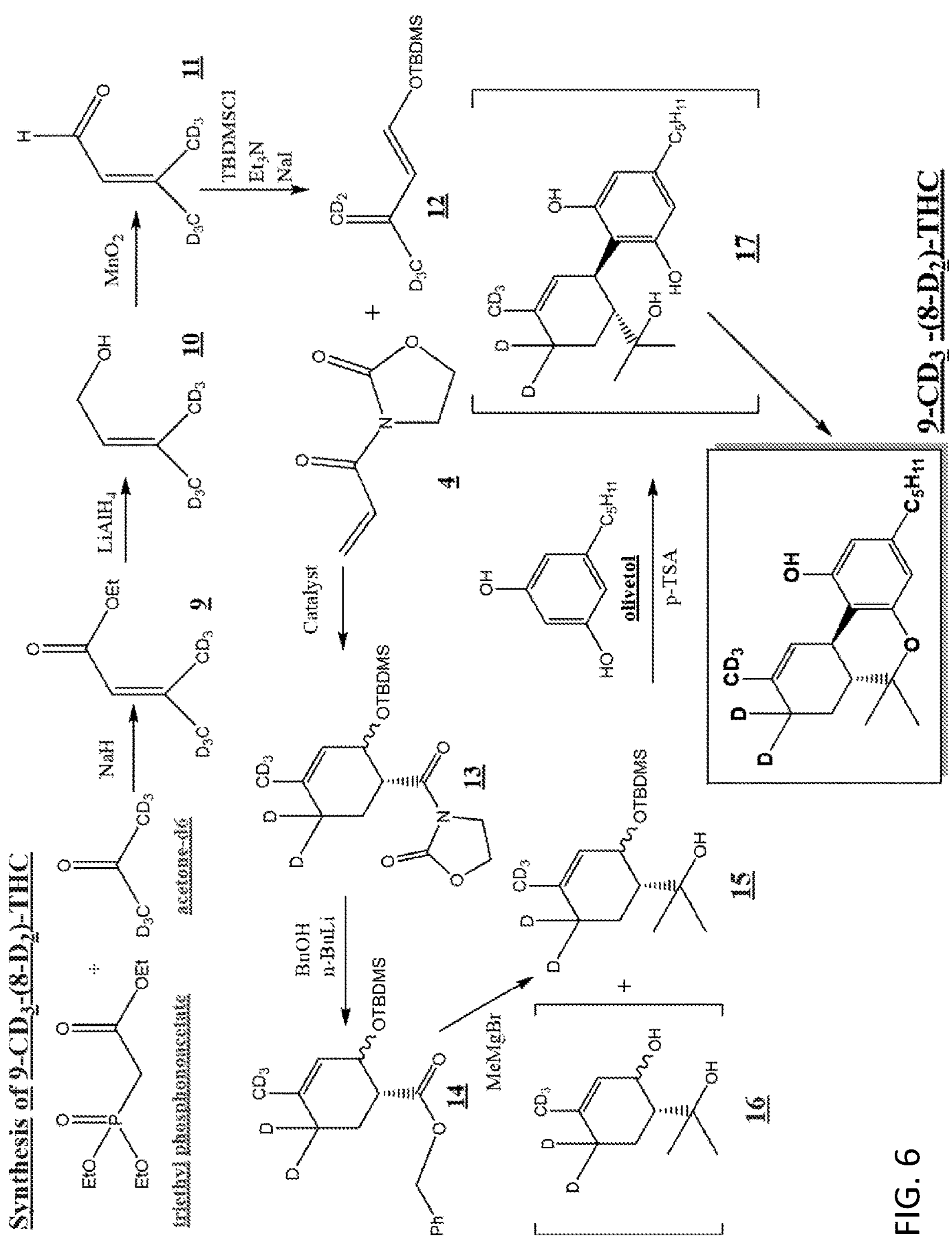
FIG. 6 represents the synthesis of 9-$CD_3$-(8-$D_2$)-THC, according to some embodiments.

The process of synthesizing 9-CD3-(8-D2) THC is described in FIG. 6.

As shown in FIG. 6, synthesis initiated with Horner-Wadsworth-Emmons reaction, to provide unsaturated ester (compound 9). Reduction to the corresponding alcohol 10, followed by mild oxidation gave the unsaturated aldehyde 11. The aldehyde reacts with t-butyldimethylchloro silane under basic conditions (Et3N), to give compound 12.

Based on Evans, D. A. et al. (*J. Am. Chem. Soc.* 1999, 121, 7582-7594), compound 12 was reacted with compound 4 in the presence of a chiral catalyst, [Cu((R,R)-t-Bu-box)]·$(SbF_6)_2$, in the Diels-alder reaction to produce compound 13. in order to obtain the correct stereochemistry at position 6a. Compound 13 underwent transesterification to give compound 14, which after Grignard reaction, gave compound 15.

Compound 15 was coupled with olivetol to give first the open-ring product 17 (using p-TSA), followed by cyclization towards the final material (using $ZnBr_2$ as a catalyst).

9

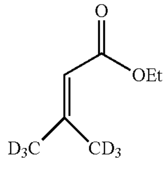

10

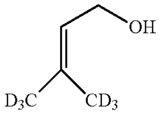

11

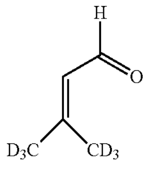

-continued

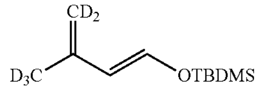

12

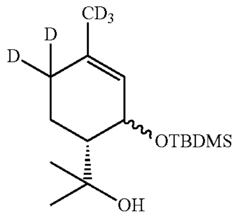

15

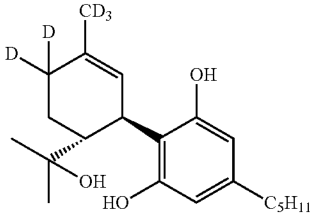

17

THC derivative 9-$CD_3$-(8-$D_2$)-THC is practically identical to the parent THC, varying only by isotopic labeling. This label does not affect the interactions with cannabinoid receptors hence maintaining THC activity. However, the isotopic modification lowers the rate of undesired metabolism, through isotopic effect, thereby slows down the formation of the undesired metabolites 11-Hydroxy THC and 11-nor-9-carboxy THC (THC acid).

Example 4. Preparation of 3-propenoyl-2-oxazolidinone

Figure 7:
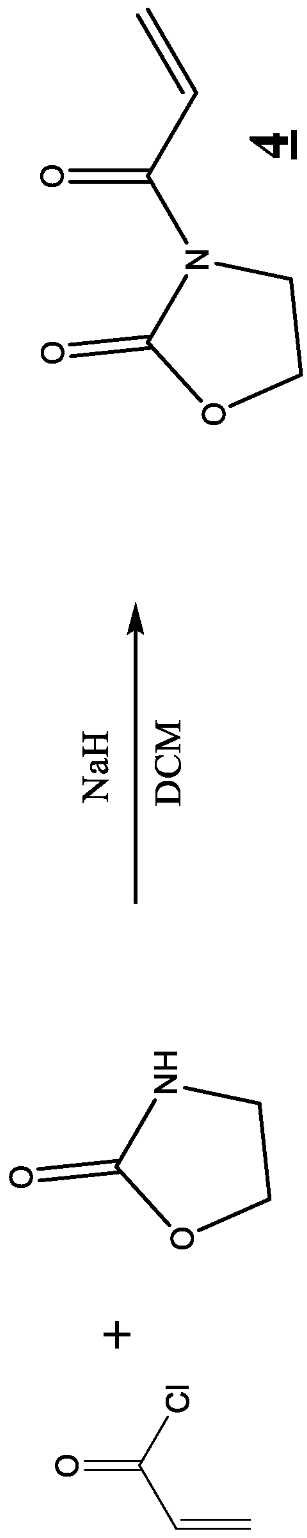
FIG. 7 represents the synthesis of 3-propenoyl-2-oxazolidinone (compound 4), according to some embodiments.

The synthesis of 3-propenoyl-2-oxazolidinone (denoted compound 4 in FIGS. 5 and 7) is presented in FIG. 7.

Oxazolidinone (4 gr, 46 mmole) was dissolved in dry DCM (60 ml) and cooled to 0° C. with stirring. To this solution, sodium hydride (60% dispersion in mineral oil, 1.9 gr, 47.5 mmole) was added and the reaction mixture was stirred at 0° C. for 20 min. Acryloyl chloride (6 ml, 74.2 mmole, 1.6 eq.) was then added dropwise and the reaction mixture was warmed to r.t. and stirred at r.t. for 18 h. To the obtained mixture, water (20 ml) was added, the reaction mixture was stirred for a few minutes and the phases were separated. The aqueous phase was washed with DCM (2×20 ml). The combined organic phases were washed with brine (30 ml), dried over $Na_2SO_4$ and filtered. After evaporation in vacuum the obtained crude residue was purified by chromatography, eluted with Hexane:EtOAc 1:3, to give 3.6 gr of compound 4, as a white solid (55% yield), having the following characteristics:

(a) $^1$H NMR (300 MHz, $CDCl_3$): δ 7.45 (dd, 1H, CHCO); 6.51 (dd, 1H, CHtrans=CHO); 5.89 (dd, 1H, CHcis=CHO); 4.46 (t, 2H, $CH_2O$); 4.08 (t, 2H, $CH_2N$);

(b) $^{13}$C NMR (300 MHz, $CDCl_3$): δ 164.3 (CON), 152.9 (CO2N), 130.8 (CHCO), 126.5 (CH═CHO), 61.7 ($CH_2O$), 42.0 ($CH_2N$).

(c) MS ($EI^+$): m/z 141 ($M\cdot^+$)

Example 5. Preparation of Compound 9

For the synthesis of compound 9 (FIG. 6) a solution of triethyl phosphonoacetate (20.0 g, 89.2 mmol) in 20 mL anhydrous ether was added dropwise via an addition funnel to a suspension of sodium hydride (4.08 g, 102 mmol, 1.14 eq., 60% dispersion in mineral oil, washed with 2×10 mL hexanes) in 80 mL anhydrous ether under $N_2$ at r.t. The reaction mixture was stirred 1 hour at r.t. then cooled to 0° C. at which time acetone-d6 (8.2 mL, 112 mmol, 1.25 eq.) was added dropwise via syringe. Upon completion of the addition, the reaction was allowed to warm at r.t. The reaction was stirred for 1 hour at r.t., then quenched with water (50 mL). The layers were separated, and the organic phase was washed with water (2×50 mL) then brine (50 mL). The combined organic layers were dried over $MgSO_4$ and filtered. Careful evaporation under vacuum (cold water in the water bath), gave 11.35 gr of the desired crude material, as a colorless fragrant liquid (compound 9) having the following characteristics:

(a) $^1$H NMR (300 MHz, $CDCl_3$) δ 5.67 (s, 1H), 4.14 (q, 2H), 1.27 (t, 3H).

(b) $^{13}$C NMR (300 MHz, $CDCl_3$) δ 166.6 (CO2Et), 156.1 (C═$CHCO_2$), 116.2 (C═$CHCO_2$), 59.3 ($CH_2CH_3$), 14.3 ($CH_2CH_3$).

Example 6. Preparation of Compound 10

For the synthesis of compound 10 (FIG. 6) lithium aluminum hydride (2.22 g, 58.4 mmol) was placed in a flame dried, three-neck, round-bottom flask under $N_2$ along with 45 mL anhydrous diethyl ether and cooled to −78° C. Crude compound 9 (11.35 g) was added dropwise via an addition funnel. After 1 hour of stirring at −78° C., the reaction was warmed to 0° C. and quenched by the dropwise addition of saturated $NH_4Cl$. The layers were separated, and the aqueous phase was extracted with ether (3×50 mL). The combined organic phases were washed with water (2×60 mL) then brine (50 mL). The organic phase was dried over $MgSO_4$ and filtered. Careful evaporation under vacuum (cold water in the water bath), gave 5.52 g of the desired crude product as a colorless very smelly liquid (compound 10) having the following characteristics:

(a) $^1$H NMR (400 MHz, $CDCl_3$) δ 5.40 (t, 1H), 4.10 (d, 2H), 1.31 (bs, 1H);

(b) $^{13}$C NMR (300 MHz, $CDCl_3$) δ 135.8 (C═$CHCH_2$), 123.8 (C═$CHCH_2$), 59.2 ($CH_2OH$),

Example 7. Preparation of Compound 11

For the synthesis of compound 11 (FIG. 6) manganese dioxide (17 g, 195 mmol) was added to crude compound 10 (5.52 g) in 80 mL methylene chloride at room temperature. The reaction mixture was stirred at reflux for 20 h (hours) then cooled at r.t. and filtered over Celite, washing with methylene chloride. Careful evaporation under vacuum (cold water in the water bath), gave 4.02 g of the desired crude material, as a colorless fragrant liquid (compound 11) having the following characteristics:

(a) $^1$H NMR (300 MHz, $CDCl_3$) δ 9.96 (d, 1H), 5.89 (d, 1H);

(b) $^{13}$C NMR (300 MHz, $CDCl_3$) δ 191.2 (HC═O), 160.7 (C═CH—HC═O), 128.3 (C═CH—HC═O)

Example 8. Preparation of Compound 12

For the synthesis of compound 12 (FIG. 6) crude compound 11 (4.02 g) was slurred in 80 mL dry ACN at r.t. with stirring and Et3N was added. The solution became clear and stirred 20 min. at r.t. Then, sodium iodide (10.0 gr, 66.6 mmol) and TBDMSCl (10.0 gr, 66.6 mmol) were added, and the mixture was stirred at 45° C. for 18 h. After cooling, pentane (100 ml) was added and the mixture. was stirred for a few min. The phases were separated in a separatory funnel and the ACN phase was washed with pentane (2×100 mL). The combined phases were washed with diluted $NaHCO_3$ solution (50 ml) then brine (50 mL). The organic phase was dried over $MgSO_4$ and filtered. Careful evaporation under vacuum gave 11.1 g of the desired crude material, which was chromatographed (Pentane:Ether) to give 4.35 gr (24% yield, for 4 stages) pure compound 12 as a colorless liquid having the following characteristics:

(a) $^1$H NMR (300 MHz, Acetone-d6 major diastereoisomer (trans)) δ 6.64 (d, 1H, CHCHOSi); 5.79 (d, 1H, CHCHOSi); 0.93 (s, 9H, $SiC(CH_3)_3$); 0.18 (s, 6H, $SiMe_2C(CH_3)_3$);

(b) $^{13}$C NMR (300 MHz, Acetone-d6) δ 143.5 (CHCHOSi), 140.7 (CCHCHO), 117.1 (CHCHO), 26.2 ($SiC(CH_3)_3$), 19.0 ($SiC(CH_3)_3$), −4.9 ($SiMe_2C(CH_3)_3$);

(c) MS (EI$^+$): m/z 203 (M·$^+$), 146 (M-(t-Bu)·$^+$).

Example 9. Preparation of Compound 13

For the synthesis of compound 13 (FIG. 6) compound 4 (273 mg, 1.94 mmol) was dissolved in prepared catalyst solution (6.0 ml, 0.0167 M, 0.1 mmol) in a round bottom flask with magnetic stirrer under Nitrogen atmosphere. After complete dissolution, compound 12 (1.47 g, 7.24 mmol, eq.) was added via syringe. The solution was stirred at room temperature for 18 h. The reaction mixture was poured directly on the top of the chromatography column and purified, to give 585 mg (88% yield) pure compound 13 as an off-white solid. NMR analysis showed a ratio of about 83:17 of the two diasterioisomers:

(a) $^1$H NMR (400 MHz, $CDCl_3$) (major diastereoisomer): δ 5.32 (d, 1H, C═CHCHOSi); 4.66 (m, 1H, CHCHOSi); 4.41 (m, 2H, $CH_2O$); 4.02 (m, 2H, $CH_2N$); 3.84 (m, 1H, CHCON); 1.95 (dd, 1H from $CH_2CD_2$); 1.67 (t, 1H from $CH_2CD_2$); 0.86 (s, 9H, $SiC(CH_3)_3$); 0.11 (s, 3H, $SiMe_2C(CH_3)_3$)); 0.03 (s, 3H, $SiMe_2C(CH_3)_3$);

(b) $^{13}$C NMR (400 MHz, $CDCl_3$, major diastereoisomer): δ 176.0 (CON), 153.2 (CO2N), 135.4 ($CD_2C$═CH), 125.7 ($CD_2C$═CH), 70.0 (CHOSi), 61.9 ($NCH_2CH_2O$), 46.8 (CHCON), 43.0 ($NCH_2CH_2O$), 25.9 ($SiCMe_3$), 25.2 ($CD_2CH_2$), 17.9 ($SiCMe_3$), −4.2 ($SiMe_2$)

(c) MS (ESI$^+$): m/z 367.20723 (MNa$^+$, found), 367.20719 (MNa$^+$, calc.)

Example 10. Preparation of Compound 14

For the synthesis of compound 14 (FIG. 6) benzyl alcohol (0.34 g, 3.4 mmol) was dissolved in dry THF (30 ml) in a round bottom flask with magnetic stirrer under Nitrogen atmosphere and the solution was cooled to −40° C. Then, n-BuLi (2.5 M in Hexane, 1.3 ml, 3.25 mmol) was added via syringe. The mixture was allowed stirring at this temperature for 30 min. and then warmed to −20° C. A pre-cooled (−20° C.) solution of compound 13 (585 mg, 1.7 mmole) in dry THF (25 ml) was added dropwise and the mixture was allowed to stir for 18 h. during it was warmed to r.t. Saturated $NH_4Cl$ solution (5 ml) was then added slowly, for quenching, the reaction mixture was stirred for 10 min, and evaporated under reduced vacuum. Ether (30 ml) was added to the residue, the phases were separated, and the aqueous phase was extracted with ether (20 ml). The combined org. phases were washed with Brine (20 ml), dried over $Na_2SO_4$ and filtered. Evaporation under reduced pressure gave crude product as colorless oil. Chromatography over silica (10% E.A. in Hexane gradually increased to 20% E.A. in Hexane) gave 297 mg (48% yield) pure compound 14, as colorless oil having the following characteristics:

(a) $^1$H NMR (400 MHz, $CDCl_3$, major diastereoisomer): δ 7.34 (m, 5H, Aryl), 5.30 (d, 1H, C═CHCHOSi); 4.66 (dd, 1H, CHCHOSi); 2.52 (ddd, 1H, CHCOOBz); 1.91 (dd, 1H from $CH_2CD_2$); 1.76 (t, 1H from $CH_2CD_2$); 0.86 (s, 9H, $SiC(CH_3)_3$); 0.07 (s, 3H, $SiMe_2C(CH_3)_3$)); 0.02 (s, 3H, $SiMe_2C(CH_3)_3$);

(b) $^{13}$C NMR (400 MHz, $CDCl_3$, major diastereoisomer): δ 175.2 (COOBz), 136.2 ($CD_2C$═CH), 128.6, 128.2, 128.1, 125.6 (Aryl carbons), 125.2 ($CD_2C$═CH), 73.1 ($Me_2COH$ CHOH), 69.5 (CHOSi), 66.3 ($OCH_2Ar$), 24.6 (CD2CH2), 25.9 ($SiCMe_3$), 18.5 ($SiCMe_3$), −4.7 ($SiMe_2$)

(c) MS (ESI$^+$): m/z 388.234 (MNa$^+$, found), 388.232 (MNa$^+$, calc.)

Example 11. Preparation of Compound 15

For the synthesis of compound 15 (FIG. 6), compound 14 (1.33 gr, 4.85 mmol) was dissolved in dry THF (30 ml) in a round bottom flask with magnetic stirrer under Nitrogen atmosphere. The solution was cooled to 0° C. and methyl magnesium bromide solution (3M in ether, 10 ml, 30 mmol, 6.19 eq.) was added via syringe. The reaction mixture was allowed to stir for 3.5 h during it was warmed to r.t. The reaction mixture was poured slowly over pre-cooled (0° C.) $NH_4Cl$ saturated solution (50 ml) and after a short stirring, the phases were separated. The aqueous phase was washed with ether (3×10 ml). The combined organic phases were washed with Brine (10 ml), dried over $Na_2SO_4$ and filtered. Evaporation under reduced pressure gave 1.1 gr of crude product as colorless oil. Chromatography over silica (50% E.A. in Hexane gradually increased to 80% E.A. in Hexane) gave 0.52 gr (68.7% yield) pure compound 15 as colorless oil. NMR analysis showed a ratio of about 83:17 of the two diastereoisomers:

(a) $^1$H NMR (400 MHz, $CDCl_3$, major diastereoisomer): δ 5.23 (d, 1H, C═CHCHOSi); 4.8 ((br s, 1H, OH), 4.47 (m, 1H, CHCHOSi); 1.66 (m, 2H, $CH_2CD_2C$); 1.27 (br s, 1H, $CHCMe_2$); 1.14 (s, 3H, Me); 1.09 (s, 3H, Me); 0.84 (s, 9H, $SiC(CH3)_3$); 0.11 (s, 6H, $SiMe_2C(CH3)_3$):

(b) $^{13}$C NMR (400 MHz, $CDCl_3$, major diastereoisomer): δ 136.2 ($CD_2C$═CH), 125.8 ($CD_2C$═CH), 73.1 (MezCOH CHOH), 72.8 (CHOSi), 50.9 ($CH_2CHCMe_2$), 30.0 (m, $CD_2CH_2$), 28.1 ($CH_2CH_2CH$═CH), 29.6 (Me), 24.3 (Me), 24.0 ($CD_2CH_2$), 21.8 (m, $CD_3$), 25.9 ($SiCMe_3$), 17.9 ($SiCMe_3$), −4.2 ($SiMe_2$);

(c) MS (EI$^+$): m/z found: 271 (M-$H_2O$)·$^+$

Example 12. Preparation of Compound 17

Figure 8:
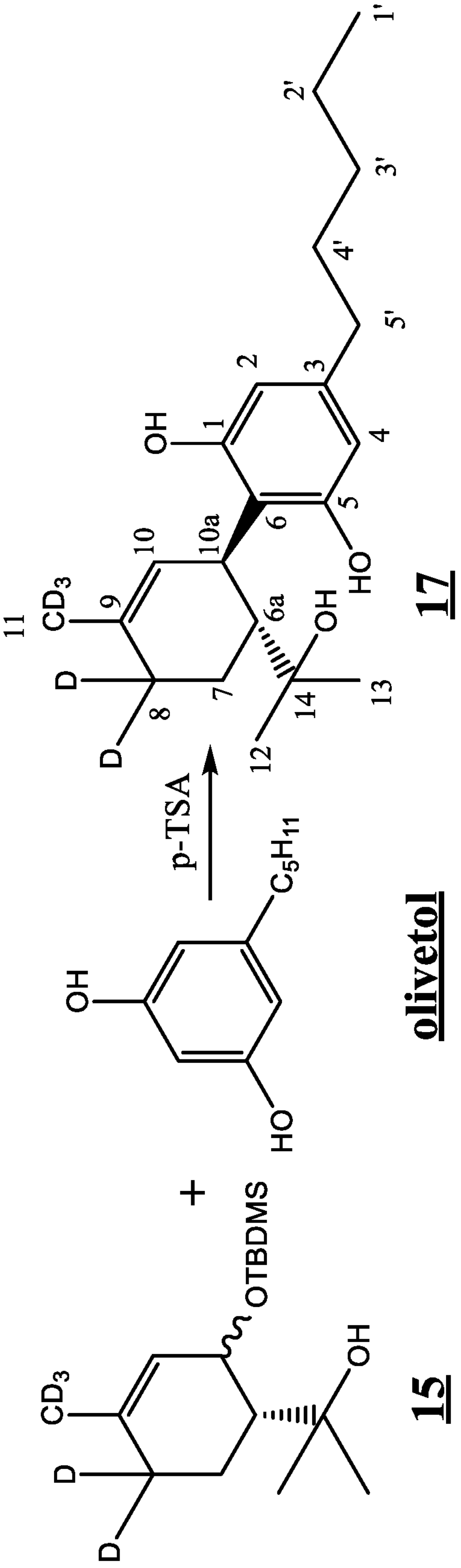
FIG. 8 represents the synthesis of compound 17, according to some embodiments.

The synthesis of compound 17 (FIG. 6), is illustrated in FIG. 8. Compound 15 (118 mg, 0.4 mmol) was dissolved in DCM (110 ml) in a round bottom flask with magnetic stirrer. Olivetol (83 mg, 0.46 mmol) was added, and the solution was cooled to 4+2° C. Then, p-TSA (46 mg, 0.24 mmol) was added and the reaction mixture. was stirred at 4±2° C. for 5 h. Saturated $NaHCO_3$ solution (20 ml) was then added slowly, for quenching. The reaction mixture was stirred for 10 min, and the phases were separated. The aqueous phase was extracted with DCM (20 ml). The combined organic phases were washed with Brine (20 ml), dried over $Na_2SO_4$ and filtered. Evaporation under reduced pressure gave crude product as colorless oil. Chromatography over silica (20% E.A. in Hexane gradually increased to 30% E.A. in Hexane) gave 59 mg (44% yield) pure compound 17, as a colorless semi solid having the following characteristics:

(a) $^1H$ NMR (400 MHz, $CDCl_3$): δ 6.51 (br s, 1H, OH); 6.32 (d, 1H, H2); 6.26 (d, 1H, H4); 5.69 (d, 1H, H10); 3.83 (dd, 1H, H10a); 2.45 (t, 2H, H5'); 1.90 (ddd, 1H, H6a); 1.81 (dd, 1H, H7); 1.58 (m, 2H, H4'); 1.31 (m, 4H, H2'+H3'); 1.24 (s, 6H, H12+H13); 0.88 (t, 2H, H5');

(b) $^{13}C$ NMR (400 MHz, $CDCl_3$): δ 156.07 (C1), 154.25 (C5), 143.53 (C3), 139.97 (C9), 123.71 (C10), 114.86 (C6), 109.56 (C2+C4), 75.14 (C14), 48.29 (C6a), 35.50 (C5'), 32.77 (C10a), 31.53 (C3'), 30.66 (C4'), 29.71 (C12), 27.72 (C12), 26.05 (C13), 22.90 (C7), 22.56 (C2'), 14.02 (C1')

(c) MS ($ESI^+$): m/z found: 338.274 ($MH^+$); calc.: 338.274

Example 13. Preparation of 9-$CD_3$-(8-$D_2$)-THC

Figure 9:
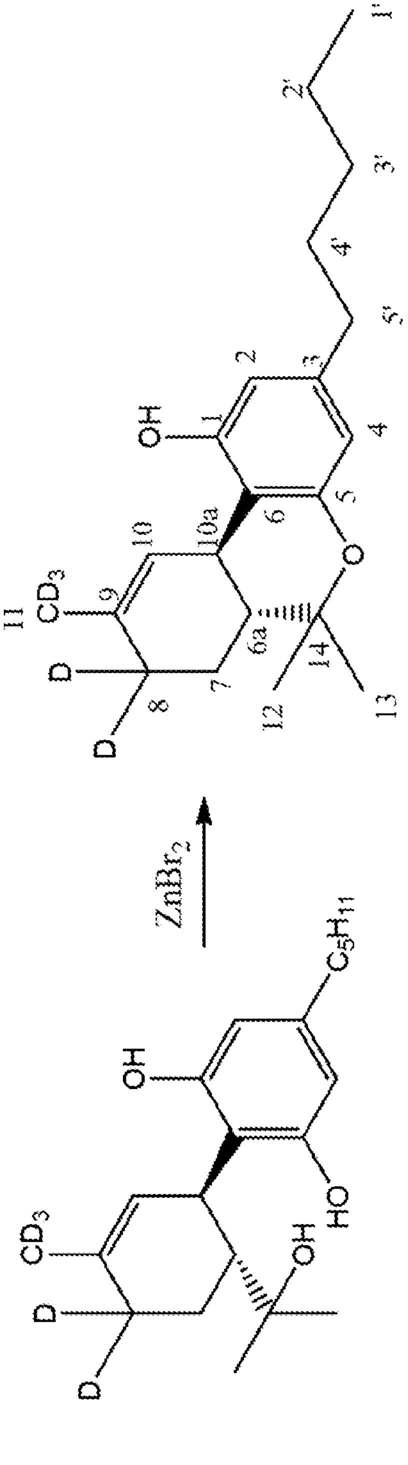
FIG. 9 represents the synthesis of 9-$CD_3$-(8-$D_2$)-THC, according to some embodiments.

The synthesis of THC derivative 9-$CD_3$-(8-$D_2$)-THC (also termed 9-$CD_3$-(8-$D_2$)-THC) is illustrated in FIG. 9.

Compound 17 (59 mg, 0.175 mmol) was dissolved in DCM (8 ml) in a round bottom flask with magnetic stirrer. $MgSO_4$ (300 mg, 2.5 mmol) was added, followed by $ZnBr_2$ (170 mg, 0.76 mmol) was added and the reaction mixture was stirred at r.t. for 4 h. Saturated $NaHCO_3$ solution (5 ml) was then added, for quenching. The reaction mixture was stirred for 5 min, and the phases were separated. The aqueous phase was extracted with DCM (5 ml). The combined organic phases were washed with Brine (5 ml) and evaporated under reduced pressure gave crude product as colorless oil. Chromatography over silica (10% E.A. in Hexane gradually increased to 30% E.A. in Hexane) gave 34 mg (61% yield) pure THC derivative 9-$CD_3$-(8-$D_2$)-THC as a colorless oil, having the following characteristics:

(a) $^1H$ NMR (400 MHz, $CDCl_3$): δ 6.30 (d, 1H, H10); 6.27 (d, 1H, H4); 6.14 (d, 1H, H2); 4.81 (br s, 1H, OH), 3.19 (dd, 1H, H10a); 2.43 (t, 2H, H5'); 1.90 (dd, 1H, 1H from H7); 1.68 (ddd, 1H, H6a); 1.56 (m, 2H, H4'); 1.41 (s, 3H, H12); 1.38 (dd, 1H, 1H from H7) 1.30 (m, 4H, H2'+H3'); 1.14 (s, 3H, Me); 1.09 (s, 3H, H13); 0.88 (t, 2H, J=7 Hz, H5');

(b) $^{13}C$ NMR (400 MHz, $CDCl_3$): δ 154.93 (C5), 154.33 (C1), 142.96 (C3), 134.38 (C9), 123.99 (C10), 110.23 (C4), 109.21 (C6), 107.09 (C2), 77.35 (C14), 45.96 (C6a), 35.02 (C5'), 33.72 (C10a), 31.66 (C3'), 30.79 (C4'), 24.0 (C1'), 27.72 (C12), 24.95 (C7), 22.68 (C2'), 19.42 (C13), 14.15 (C1');

(c) MS ($ESI^+$): m/z found: 320.263 ($MH^+$); calc.: 320.263.

Example 14. Preparation of 9-$CF_3$-THC

Figure 10:
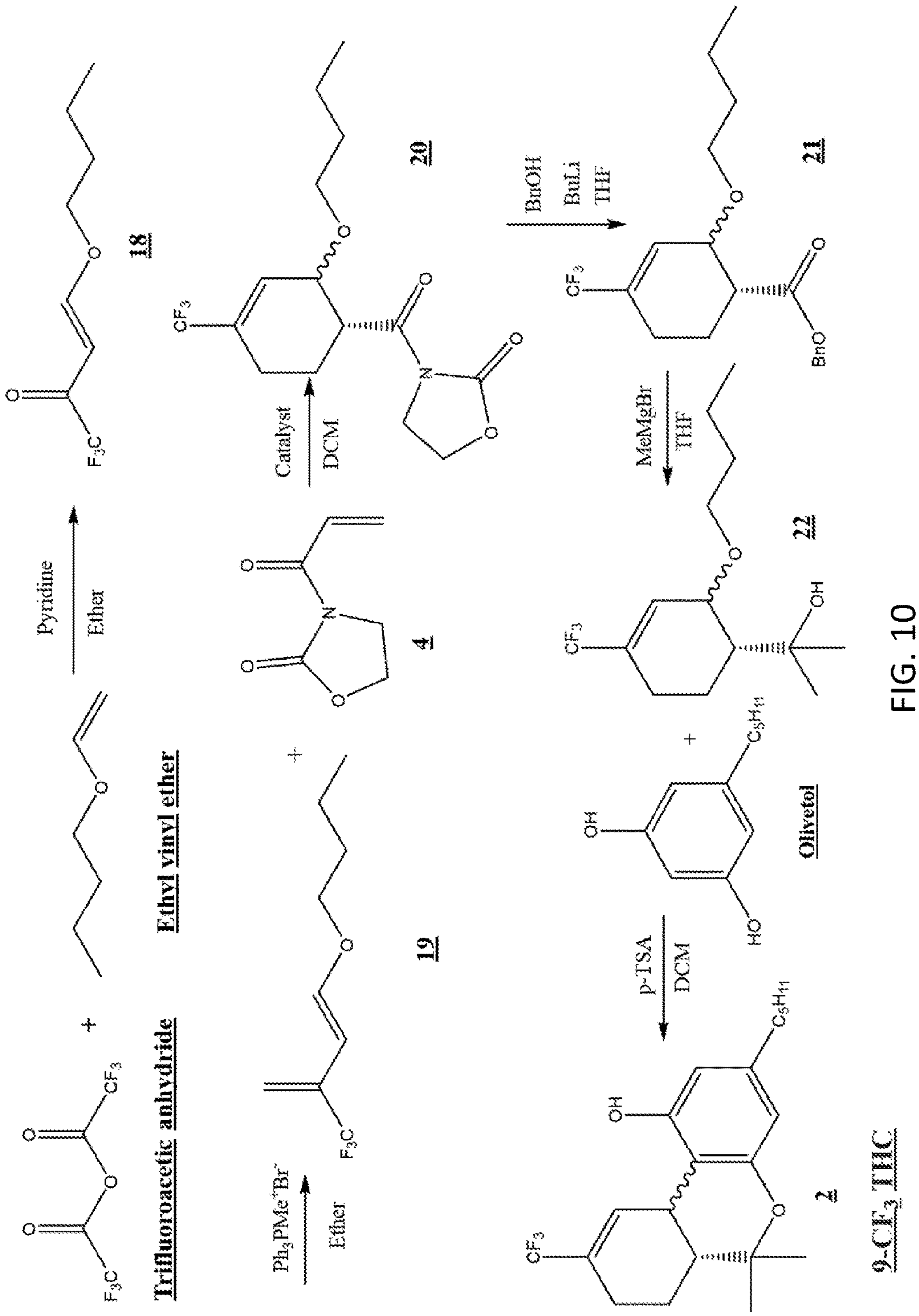
FIG. 10 represents the synthesis of 9-$CF_3$-THC, according to some embodiments.

The synthesis of THC derivative 9-$CF_3$-THC is illustrated in FIG. 10. The synthesis of 9-$CF_3$-THC includes the following steps:

Ethyl vinyl ether and Trifluoroacetic anhydride reacted smoothly in the presence of Pyridine, to give the conjugated trifluoromethyl ketone compound 18, which after a common Wittig reaction with methyl triphenylphosphonium bromide, gave the diene compound 19. Based on Evans, D. A. et al, a chiral catalyst, [Cu((R,R)-t-Bu-box)]·(SbF6)2 was applied in the Diels-alder reaction together with compound 4 towards compound 20, in order to obtain the correct stereochemistry at position 6a. Compound 20 underwent transesterification to give compound 21, which after Grignard reaction, gave compound 22. Compound 22, was coupled with olivetol in acidic conditions, followed by cyclization, towards the final compound, 9-$CF_3$ THC.

The THC derivative 9-Trifluoromethyl THC is similar to the parent compound, with replacement of the 11-Me group with isosteric trifluoromethyl group. Thus, it can interact with the target receptor in a similar manner to the parent THC, but does not interact with the metabolic enzymes.

Example 15. Evaluation of the Biological Activity—Nociception Assays

Mechanical sensitivity was evaluated by measuring the changes in tactile sensitivity in the hind paw of mice, using an Electronic Von-Frey apparatus (EVF). Withdrawal thresholds were measured, using the EVF apparatus, first at baseline (time=0) and then following drug, in a few periods after administration, by applying an accurate force on specific areas of the skin and measuring the needed force for the mouse to lift its paw.

Paclitaxel was utilized for the stimulation of a chemotherapy-induced neuropathic pain. Paclitaxel is anti-cancer chemotherapy drug classified as a "plant alkaloid" and an "antimicrotubule agent".

Paclitaxel and each synthetic THC derivative were dissolved in a mixture of 0.9% Saline solution:Ethanol:Cremophore in a ratio of 18:1:1. In the beginning, each material was dissolved in Ethanol and then the same volume of Cremophore was added. After short stirring, 18 volumes of saline solution were added.

Mice were divided into three groups of 8 mice each, as follows:

(a) Group no. 1—Morphine as positive control;

(b) Group no. 2—synthetic THC derivative 9-$CD_3$-(8-$D_2$)-THC;

(c) Group no. 3—synthetic THC derivative 9-Desmethyl THC.

A portion of Paclitaxel was administered to each mouse by i.p. injection, on days 1, 3, 5 and 7 from the beginning of the experiment. At day 8, withdrawal thresholds were measured first at baseline (time=0), thereafter each mouse received a single portion of a drug substance, at 5 mg/Kg body weight concentration, by oral gavage and measurements took place.

The first checking point was 1 hour after administration of each drug. For every mouse, its threshold for the pain perception in which it removes its hind paw after the stabbing of the Von-Frey hair has been checked. Needed force (in gram force units) was measured each time and was recorded for every checking. This test was repeated 5 times for each mouse consecutively.

This procedure was repeated for all the three groups. The next checking point was 3 hours after administration, where the last withdrawal thresholds measurements were performed on the next morning, on day 9, which was 24 hours after administration.

Morphine was utilized as a positive control where group no. 1 mice received morphine (dissolved in a saline solution (0.9%) and injected subcutaneously) as an analgesic agent, prior to the mechanical sensitivity tests. The results (units are expressed in gram force), are summarized in tables 1-4.

TABLE 1

| Withdrawal test at t = 0 | | | | | | | | | | |
|---|---|---|---|---|---|---|---|---|---|---|
| Baseline | | t = 0 | | | | | | | All group | |
| Group | Animal | test 1 | test 2 | test 3 | test 4 | test 5 | test 6 | Average | average | Sd |
| 1 | 1 | 7.9 | 4.5 | 6.8 | 7.5 | 5.1 | | 6.36 | 5.82 | 1.213 |
| | 2 | 4.8 | 7.1 | 4.5 | 5.6 | 6.3 | | 5.66 | | 1.023 |
| | 3 | 7 | 7.8 | 6.7 | 7 | 5.6 | | 6.82 | | 1.142 |
| | 4 | 5.1 | 4.2 | 5.6 | 4.9 | 4.6 | | 4.88 | | 1.042 |
| | 5 | 4.1 | 5.0 | 5.2 | 4.3 | 7.9 | | 5.30 | | 1.449 |
| | 6 | 4.8 | 6.0 | 5.2 | 6.6 | 8.7 | | 6.26 | | 1.635 |
| | 7 | 4.5 | 4.5 | 9.1 | 4.3 | 6.1 | | 5.70 | | 1.551 |
| | 8 | 4.7 | 4.6 | 7.4 | 4.5 | 6.7 | | 5.58 | | 1.272 |
| 2 | 9 | 4.8 | 7.9 | 5.5 | 6.7 | 4.3 | | 5.84 | 5.42 | 1.206 |
| | 10 | 5.5 | 4.0 | 4.1 | 5.4 | 6.6 | | 5.12 | | 0.848 |
| | 11 | 4.2 | 6.1 | 4.6 | 4.4 | 5.2 | | 4.90 | | 0.533 |
| | 12 | 5.0 | 4.6 | 4.6 | 4.5 | 4.3 | | 4.60 | | 1.292 |
| | 13 | 7.3 | 8.1 | 5.0 | 1.1 | 6.1 | | 6.12 | | 1.323 |
| | 14 | 6.8 | 4.3 | 5.6 | 7.5 | 7.1 | | 6.26 | | 1.144 |
| | 15 | 7.1 | 4.5 | 5.6 | 6.6 | 4.6 | | 5.68 | | 1.021 |
| | 16 | 4.8 | 4.0 | 5.1 | 4.0 | 6.1 | | 4.80 | | 1.069 |
| 3 | 17 | 4.1 | 4.9 | 6.4 | 4.5 | 7.3 | | 5.44 | 6.18 | 1.874 |
| | 18 | *11.7 | 7.9 | 9.9 | 5.2 | 4.2 | | 6.80 | | 1.959 |
| | 19 | 7.7 | 6.9 | 4.0 | *29.7 | 4.9 | 11.2 | 5.88 | | 1.339 |
| | 20 | 6.5 | *23.9 | 6.6 | 8.0 | *14.4 | 4.4 | 7.03 | | 0.934 |
| | 21 | 6.7 | 4.6 | 6.0 | 7.2 | 5.9 | | 6.08 | | 0.918 |
| | 22 | 4.8 | 4.8 | 5.8 | 6.8 | 4.7 | | 5.38 | | 1.188 |
| | 23 | 7.5 | 6.0 | 7.8 | 4.1 | 5.5 | | 6.18 | | 1.480 |
| | 24 | 8.8 | 4.7 | 5.6 | *13.6 | 7.4 | | 6.63 | | 1.588 |

TABLE 2

| Withdrawal test at t = 1 | | | | | | | | | | | |
|---|---|---|---|---|---|---|---|---|---|---|---|
| — | | t = 1 h | | | | | | | All group | Change from | |
| Group | Animal | test 1 | test 2 | test 3 | test 4 | test 5 | test 6 | Average | average | b.l. | Sd |
| 1 | 1 | 4.7 | 7.6 | 4.4 | 4.2 | 9.2 | | 6.02 | 6.21 | +6.7% | 2.014 |
| | 2 | 4.4 | 4.2 | 4.9 | 5.3 | 7.5 | | 5.26 | | | 1.184 |
| | 3 | 5.6 | 6.0 | *10.2 | 4.4 | 5.8 | | 5.45 | | | 0.622 |
| | 4 | 4.4 | 6.5 | 4.2 | 9.1 | 4.2 | | 5.68 | | | 1.918 |
| | 5 | 8.5 | 4.3 | 8.1 | 8.3 | 9.8 | | 7.80 | | | 1.848 |
| | 6 | 8.4 | *10.3 | *10.5 | 7.4 | 5.7 | | 7.17 | | | 1.115 |
| | 7 | 5.2 | 7.9 | 4.5 | 6.5 | 9.0 | | 6.62 | | | 1.663 |
| | 8 | 5.9 | 8.3 | 4.3 | 5.0 | 4.9 | | 5.68 | | | 1.406 |
| 2 | 9 | 4.7 | 4.1 | 4.2 | 4.3 | 5.4 | | 4.54 | 5.68 | +4.8% | 0.476 |
| | 10 | 4.8 | 5.8 | 6.9 | 4.5 | 8.7 | | 6.14 | | | 1.532 |
| | 11 | 6.0 | 6.5 | 7.7 | 5.9 | 7.7 | | 6.76 | | | 0.794 |
| | 12 | 5.0 | 4.0 | 5.3 | 6.7 | 5.2 | | 5.24 | | | 0.864 |
| | 13 | 4.5 | 4.8 | 7.5 | 7.1 | 4.3 | | 5.64 | | | 1.371 |
| | 14 | 6.1 | 4.6 | 4.3 | 4.7 | 4.7 | | 4.88 | | | 0.627 |
| | 15 | 6.0 | 8.9 | 6.1 | 5.3 | 4.5 | | 6.16 | | | 1.485 |
| | 16 | 7.1 | 5.6 | 4.9 | 4.2 | 8.5 | | 6.06 | | | 1.553 |
| 3 | 17 | 4.0 | 6.1 | 4.4 | 5.3 | 4.3 | | 4.82 | 5.55 | −10.2% | 0.773 |
| | 18 | 7.2 | 4.7 | 5.1 | 5.3 | 6.8 | | 5.82 | | | 0.991 |
| | 19 | 5.1 | 9.8 | 4.2 | 5.7 | 4.4 | 6.3 | 5.84 | | | 2.050 |
| | 20 | 4.0 | 9.4 | 6.2 | 4.0 | 7.4 | 5.3 | 6.20 | | | 2.067 |
| | 21 | 4.3 | 6.7 | 5.7 | 4.3 | 4.6 | | 5.12 | | | 0.943 |
| | 22 | 4.9 | 5.7 | 4.2 | 4.3 | 6.8 | | 5.18 | | | 0.970 |
| | 23 | 7.3 | 6.1 | 7.0 | 5.4 | 4.1 | | 5.98 | | | 1.155 |
| | 24 | 5.3 | 4.0 | 7.7 | 4.5 | 5.6 | | 5.42 | | | 1.273 |

TABLE 3

| Withdrawal test at t = 3 h | | | | | | | | | | | |
|---|---|---|---|---|---|---|---|---|---|---|---|
| — | | t = 3 h | | | | | | | All group | Change from | |
| Group | Animal | test 1 | test 2 | test 3 | test 4 | test 5 | test 6 | Average | average | b.l. | Sd |
| 1 | 1 | 6.4 | 4.4 | 4.3 | 5.3 | 5.2 | | 5.12 | 5.79 | −0.5% | 0.757 |
| | 2 | 5.3 | 5.5 | 8.4 | 6.4 | 6.1 | | 6.34 | | | 1.104 |
| | 3 | 5.4 | 5.3 | 4.5 | 5.8 | 5.7 | | 5.34 | | | 0.459 |
| | 4 | 7.2 | 5.5 | 6.3 | 5.5 | 6.9 | | 6.28 | | | 0.700 |
| | 5 | 5.3 | 6.8 | 4.4 | 4.9 | 8.6 | 7.0 | 6.00 | | | 1.527 |
| | 6 | *11.6 | 4.3 | 4.3 | 4.6 | 5.5 | 4.5 | 4.68 | | | 0.492 |
| | 7 | 6.6 | 6.1 | 4.9 | 4.3 | 5.6 | | 5.50 | | | 0.822 |
| | 8 | 5.6 | 5.9 | 5.2 | 7.0 | 4.6 | | 5.66 | | | 0.799 |
| 2 | 9 | 4.6 | 5.9 | 4.8 | 4.7 | 5.8 | | 5.16 | 5.67 | +4.6% | 0.568 |
| | 10 | 4.4 | 5.4 | 6.4 | 9.2 | 6.7 | 4.1 | 6.42 | | | 1.608 |
| | 11 | 4.7 | 5.0 | 5.6 | 4.3 | 4.0 | | 4.72 | | | 0.556 |
| | 12 | 6.9 | 5.1 | *12.8 | 5.9 | 6.4 | 4.9 | 6.08 | | | 0.665 |
| | 13 | 8.2 | 5.1 | 4.7 | 6.2 | 4.0 | 4.3 | 5.64 | | | 1.465 |
| | 14 | 4.4 | 9.2 | 4.9 | 6.6 | 4.5 | 4.9 | 5.92 | | | 1.821 |
| | 15 | 7.6 | 7.2 | 5.6 | 5.2 | 4.8 | | 6.08 | | | 1.114 |
| | 16 | 4.5 | 6.5 | 5.6 | 4.6 | 5.3 | | 5.30 | | | 0.729 |
| 3 | 17 | 7.4 | 5.1 | 5.4 | 4.1 | 4.7 | | 5.34 | 5.43 | −12.1% | 1.118 |
| | 18 | 5.0 | 4.6 | 4.2 | 5.0 | 6.3 | | 5.02 | | | 0.705 |
| | 19 | 4.8 | 4.8 | 5.8 | 5.4 | 4.2 | | 5.00 | | | 0.551 |
| | 20 | 4.3 | 4.8 | 5.2 | 9.5 | 4.3 | 4.4 | 5.62 | | | 1.969 |
| | 21 | 4.5 | 8.6 | 4.0 | 4.9 | 6.5 | 4.9 | 5.70 | | | 1.675 |
| | 22 | 4.6 | 4.7 | 4.0 | 6.0 | 6.8 | | 5.22 | | | 1.024 |
| | 23 | 7.0 | 8.6 | 4.0 | 4.2 | 4.7 | 4.9 | 5.70 | | | 1.802 |
| | 24 | 6.8 | 5.5 | 4.6 | 5.4 | 7.0 | | 5.86 | | | 0.907 |

TABLE 4

| Withdrawal test at t = 24 h | | | | | | | | | | | |
|---|---|---|---|---|---|---|---|---|---|---|---|
| — | | t = 24 h | | | | | | | All group | Change from | |
| Group | Animal | test 1 | test 2 | test 3 | test 4 | test 5 | test 6 | Average | average | b.l. | Sd |
| 1 | 1 | 6.9 | 6.0 | 4.8 | 4.7 | 8.0 | | 6.08 | 5.09 | −12.5% | 1.258 |
| | 2 | 4.0 | 4.7 | 5.1 | 4.6 | 4.3 | | 4.54 | | | 0.372 |
| | 3 | 5.4 | 4.0 | 4.2 | 7.4 | 4.0 | | 5.00 | | | 1.308 |
| | 4 | 5.2 | 4.7 | 4.5 | *12.9 | 6.5 | 6.5 | 5.23 | | | 0.779 |
| | 5 | 4.0 | 5.2 | 6.5 | 4.0 | 4.3 | | 4.80 | | | 0.957 |
| | 6 | 4.3 | 5.3 | 4.1 | 4.1 | 9.4 | 4.3 | 5.44 | | | 2.029 |
| | 7 | 5.2 | 5.8 | 4.1 | 6.7 | 4.6 | | 5.28 | | | 0.911 |
| | 8 | 4.1 | 4.7 | 4.0 | 4.7 | 4.1 | | 4.32 | | | 0.312 |
| 2 | 9 | 6.0 | 4.6 | 4.6 | 4.3 | 4.0 | | 4.70 | 5.28 | −2.6% | 0.687 |
| | 10 | 7.5 | 6.0 | 4.2 | 4.0 | 8.1 | | 5.96 | | | 1.667 |
| | 11 | 4.0 | 4.0 | 4.0 | 6.8 | 4.0 | | 4.56 | | | 1.120 |
| | 12 | 7.6 | 7.5 | 5.6 | *10.3 | 4.6 | 4.5 | 6.33 | | | 1.275 |
| | 13 | 5.0 | 6.5 | 4.0 | 4.3 | 5.1 | | 4.98 | | | 0.866 |
| | 14 | 4.4 | 5.3 | 5.4 | 6.8 | 4.7 | | 5.32 | | | 0.828 |
| | 15 | 4.9 | 5.7 | 5.3 | 4.1 | 4.0 | | 4.80 | | | 0.663 |
| | 16 | 4.5 | 5.0 | 6.8 | 5.2 | 6.3 | | 5.56 | | | 0.855 |
| 3 | 17 | 5.4 | 6.9 | 8.8 | 4.4 | 7.4 | | 6.58 | 5.36 | −13.3% | 1.539 |
| | 18 | 5.0 | 4.1 | 4.1 | 6.2 | 4.6 | | 4.80 | | | 0.777 |
| | 19 | 4.2 | 4.7 | 4.1 | 8.1 | *10.0 | | 5.28 | | | 1.647 |
| | 20 | 7.0 | 4.1 | 4.7 | 9.0 | 5.8 | | 6.12 | | | 1.747 |
| | 21 | 4.2 | 4.1 | 4.2 | 5.0 | 7.3 | | 4.96 | | | 1.214 |
| | 22 | 5.0 | 5.6 | 4.0 | 5.1 | 4.0 | | 4.74 | | | 0.637 |
| | 23 | 4.2 | 4.4 | 5.6 | 7.6 | 4.0 | | 5.16 | | | 1.341 |
| | 24 | 7.1 | 4.5 | 6.1 | 4.0 | 4.6 | | 5.26 | | | 1.157 |

As shown in tables 1-4, most of the results are within the range of 4-8 gram force. The tests described in this example are complicated and depend on numerous factors. Accordingly, results above 10.0 gram force (marked with an asterisk) were not included in the evaluation of the experimental data. In cases of exceptional results, an additional test was performed mouse (test 6) in order to assure the exceptional result.

Table 2 shows that in the first group at 1 hour after administration of morphine, there is an average increase of 6.7% in the withdrawal thresholds of all the mice of this group, compared to a minor average increase of 4.8% in the withdrawal thresholds of the mice of the second group, which had been administered with 9-$CD_3$-(8-$D_2$)-THC. However, the third group, which had been administered with 9-desmethyl-THC, showed an average decrease of 10.2% in the withdrawal thresholds of all the mice.

According to Table 3 at 3 hours after administration of morphine, there is a retreat and the average result is about the same as the baseline (−0.5%), where in the second group which had been administered with 9-$CD_3$-(8-$D_2$)-THC, an increase of 4.6% in the Withdrawal thresholds, compared to baseline, has been observed.

In the third group, which had been administered with 9-desmethyl-THC, there is another decrease of 12.1% compared to baseline, in the withdrawal thresholds of all the mice.

Finally, at 24 hours after administration (Table 4), an average decrease is seen, proportionally in all the 3 groups (−12.5%, −2.6%, −13.3% respectively).

In summary, the preliminary data indicates that the synthetic THC derivative 9-$CD_3$-(8-$D_2$)-THC exhibits better analgesic properties, at 3 hours after administration, in comparison to morphine (−0.5% and +4.6%, respectively) and even 24 hours after administration, it still exhibited some analgesic effect in comparison to morphine (−12.5% and −2.6%, respectively).

In view of the preliminary Von-Frey study the experiments are also repeated with rats rather than with mice, due to their larger paws to optimize reproducibility.

In view of the EVF results (Tables 1-4), 9-$CD_3$-(8-$D_2$)-THC was further evaluated.

Example 16. Evaluation of the Biological Activity-Hot Plate Assays

Another type of nociception test is a hot plate test (assay). In the hot plate assays, the synthetic THC derivative (9-$CD_3$-(8-$D_2$)-THC) in comparison to the natural THC (inner control) were evaluated. Mice were divided into 8 groups, 6 mice in every group. Each compound was orally administered, the two THC compounds in three different concentrations and morphine in one concentration. Morphine sulfate (dissolved in 0.9% saline) was administered to a single group (group A), in a concentration of 5 mg/kg. A vehicle solution (0.9% saline solution:ethanol:cremophore 18:1:1) was administered to another group (group B). The two tested drugs (compounds), THC and its deuterated derivative were administered at the following concentrations: high concentration of 8 mg/kg of body weight (groups C+D), medium concentration of 4 mg/kg (groups E+F) and low concentration of 2 mg/kg (groups G+H). In order to prepare the solutions of the evaluated drugs, each material was first dissolved in ethanol, and thereafter the same volume of cremophore was added. After short stirring, 18 volumes of 0.9% saline solution were added.

The analgesic activity and body temperature were measured on each mouse, after 0.5, 3, 6 and 24 hours (the latter for half of each group, ca. 3 mice) from drug administration. Measurements of the analgesic activity were performed by placing each mouse on a preheated hot plate (55±0.2° C.) and determining withdrawal reflex latency (WRL, the time passed from placing the mouse on the hot plate until the time it either licked its hind paw, shook it or jumped). At each time point, a special rectal thermometer was first used, to measure the body temperature. The results of groups A-H are summarized in Table 5.

TABLE 5

Hot plate results - groups A-H

| | | | t = 0 | | t = 0.5 h | | t = 3 h | | t = 6 h |
|---|---|---|---|---|---|---|---|---|---|
| Group | Animal # | Drug | Time (sec.) | Avg. 6 mice | Time (sec.) | Avg. 6 mice | Time (sec.) | Avg. 6 mice | Time (sec.) |
| A | 1 | Morphine | 10.5 | 11.37 | 12.4 | 14.43 | 14.5 | 14.05 | 12.0 |
| | 2 | | 10.7 | | 11.1 | | 8.5 | | 6.5 |
| | 3 | | 9.9 | | 15.7 | | 16.8 | | 12.7 |
| | 4 | | 8.4 | | 13.1 | | 11.4 | | 8.0 |
| | 5 | | 15.2 | | 10.5 | | 20.5 | | 26.6 |
| | 6 | | 13.5 | | 23.8 | | 12.6 | | 19.7 |
| B | 7 | Vehicle | 9.0 | 9.47 | 6.0 | 6.78 | 8.9 | 10.90 | 9.4 |
| | 8 | | 12.6 | | 7.8 | | 11.9 | | 9.4 |
| | 9 | | 8.1 | | 5.1 | | 13.9 | | 13.8 |
| | 10 | | 7.8 | | 9.1 | | 4.9 | | 9.7 |
| | 11 | | 8.3 | | 7.4 | | 7.3 | | 11.4 |
| | 12 | | 11.0 | | 5.3 | | 18.5 | | 11.7 |
| C | 13 | THC | 8.4 | 7.90 | 15.2 | 13.22 | 21.6 | 12.45 | 13.2 |
| | 14 | 8 mg/Kg | 6.2 | | 11.1 | | 9.0 | | 9.2 |
| | 15 | | 8.0 | | 14.2 | | 9.8 | | 6.8 |
| | 16 | | 7.0 | | 6.7 | | 9.5 | | 16.7 |
| | 17 | | 7.2 | | 19.6 | | 12.5 | | 17.0 |
| | 18 | | 10.6 | | 12.5 | | 12.3 | | 9.3 |
| D | 19 | THC-d5 | 6.9 | 9.18 | 19.9 | 15.42 | 30.0 | 22.10 | 6.4 |
| | 20 | 8 mg/Kg | 9.7 | | 24.5 | | 30.0 | | 9.8 |
| | 21 | | 13.2 | | 11.1 | | 6.0 | | 11.5 |
| | 22 | | 7.0 | | 17.5 | | 30.0 | | 7.1 |
| | 23 | | 11.0 | | 10.1 | | 26.2 | | 13.4 |
| | 24 | | 7.3 | | 9.4 | | 10.4 | | 2.3 |
| E | 25 | THC | 11.1 | 10.17 | 11.3 | 12.48 | 17.3 | 11.00 | 12.1 |
| | 26 | 4 mg/Kg | 13.7 | | 19.8 | | 8.0 | | 2.4 |
| | 27 | | 5.3 | | 6.3 | | 9.3 | | 3.0 |
| | 28 | | 15.0 | | 14.0 | | 6.9 | | 14.0 |
| | 29 | | 10.3 | | 12.2 | | 13.9 | | 14.0 |
| | 30 | | 5.6 | | 11.3 | | 10.6 | | 8.0 |
| F | 31 | THC-d5 | 6.1 | 8.33 | 19.2 | 14.03 | 17.5 | 13.77 | 8.7 |
| | 32 | 4 mg/Kg | 8.0 | | 10.3 | | 11.8 | | 19.9 |
| | 33 | | 9.3 | | 13.0 | | 12.1 | | 12.1 |
| | 34 | | 5.0 | | 9.5 | | 9.2 | | 8.3 |

TABLE 5-continued

Hot plate results - groups A-H

| | | | | | | | | | |
|---|---|---|---|---|---|---|---|---|---|
| | 35 | | 8.4 | | 15.8 | | 12.5 | | 22.5 |
| | 36 | | 13.2 | | 16.4 | | 19.5 | | 20.8 |
| G | 37 | THC | 8.0 | 7.45 | 5.7 | 7.38 | 9.5 | 9.77 | 13.5 |
| | 38 | 2 mg/Kg | 6.3 | | 11.5 | | 8.5 | | 6.3 |
| | 39 | | 8.2 | | 8.9 | | 18.0 | | 12.5 |
| | 40 | | 12.8 | | 9.2 | | 10.4 | | 8.7 |
| | 41 | | 3.5 | | 3.2 | | 5.3 | | 6.6 |
| | 42 | | 5.9 | | 5.8 | | 6.9 | | 11.0 |
| H | 43 | THC-d5 | 7.0 | 9.23 | 9.4 | 9.52 | 7.2 | 10.97 | 9.3 |
| | 44 | 2 mg/Kg | 11.0 | | 9.3 | | 12.1 | | 14.5 |
| | 45 | | 6.2 | | 8.9 | | 8.5 | | 4.5 |
| | 46 | | 5.8 | | 10.9 | | 19.3 | | 15.8 |
| | 47 | | 16.0 | | 12.0 | | 13.1 | | 8.9 |
| | 48 | | 9.4 | | 6.6 | | 5.6 | | 7.4 |

| | | t = 6 h | t = 24 h | | | | | |
|---|---|---|---|---|---|---|---|---|
| | Animal | Avg. | Time | Avg. | P value (rel. t = 0) | | | |
| Group | # | 6 mice | (sec.) | 3 mice | t = 0.5 h | t = 3 h | t = 6 h | t = 24 h |
| A | 1 | 14.25 | 2.4 | 5.8 | 0.101 | 0.062 | 0.124 | 0.067 |
| | 2 | | 9.0 | | | | | |
| | 3 | | 5.9 | | | | | |
| | 4 | | | — | | | | — |
| | 5 | | | | | | | |
| | 6 | | | | | | | |
| B | 7 | 10.9 | 6.7 | 7.6 | 0.025 | 0.220 | 0.146 | 0.074 |
| | 8 | | 12.0 | | | | | |
| | 9 | | 4.0 | | | | | |
| | 10 | | | — | | | | — |
| | 11 | | | | | | | |
| | 12 | | | | | | | |
| C | 13 | 12.03 | 8.1 | 10.27 | 0.016 | 0.027 | 0.048 | 0.252 |
| | 14 | | 15.7 | | | | | |
| | 15 | | 7.0 | | | | | |
| | 16 | | | — | | | | — |
| | 17 | | | | | | | |
| | 18 | | | | | | | |
| D | 19 | 8.42 | 30.0 | 20.6 | 0.047 | 0.025 | 0.240 | 0.277 |
| | 20 | | Died | | | | | |
| | 21 | | 11.2 | | | | | |
| | 22 | | | — | | | | — |
| | 23 | | | | | | | |
| | 24 | | | | | | | |
| E | 25 | 8.92 | 13.7 | 10.43 | 0.056 | 0.376 | 0.297 | 0.376 |
| | 26 | | 12.8 | | | | | |
| | 27 | | 4.8 | | | | | |
| | 28 | | | — | | | | — |
| | 29 | | | | | | | |
| | 30 | | | | | | | |
| F | 31 | 15.38 | 5.2 | 14.27 | 0.009 | 0.004 | 0.009 | 0.130 |
| | 32 | | 21.5 | | | | | |
| | 33 | | 16.1 | | | | | |
| | 34 | | | — | | | | — |
| | 35 | | | | | | | |
| | 36 | | | | | | | |
| G | 37 | 9.77 | 7.8 | 6.53 | 0.480 | 0.109 | 0.094 | 0.289 |
| | 38 | | 7.4 | | | | | |
| | 39 | | 4.4 | | | | | |
| | 40 | | | — | | | | — |
| | 41 | | | | | | | |
| | 42 | | | | | | | |
| H | 43 | 10.07 | 7.9 | 8.3 | 0.305 | 0.263 | 0.371 | 0.407 |
| | 44 | | 9.5 | | | | | |
| | 45 | | 7.5 | | | | | |
| | 46 | | | — | | | | — |
| | 47 | | | | | | | |
| | 48 | | | | | | | |

It can be seen in Table 5, that 0.5 h after drug administration in groups A, C and D, there was a significant increase in the average WRL of the six mice in every group, in comparison to the baseline tests at t=0. While morphine (group A) elicited a mild average increase of 26.9% (14.43 sec. compared to 11.37 sec), administration of THC (group C) and $CD_3$-($8D_2$)-THC (group D), lead to much larger increase of 67.3% and 67.6%, respectively (13.22 sec. compared to 7.90 sec in group C and 15.42 sec. compared to 9.2 sec in group D). The calculated P value, based on a T test was 0.016 for group C and 0.047 for group D (P value≤0.05). At 3 h after drug administration, a very slight decrease (compared to 0.5 h) in the average WRL in groups A, and C (+23% and +57.5% respectively, compared to t=0 at baseline) was observed. However, in group D a significant increase of 140% in the WRL (22.1 sec. compared to 9.2 sec. at baseline) was noticed. The calculated P value at this stage, based on a T test, was 0.027 for group C and 0.025 for group D, indicating statistical significance. It was furthermore observed in the results of group D, that 3 out of the 6 mice in the group expressed the maximum result of 30 seconds without any response, which was the cut-off limit for this test. At 6 h after drug administration, a slight but not significant increase in the WRL in group A was observed (+25% compared to +23% at 3 h) as well as a slight decrease in the average WRL of group C (+52% compared to +57.5% at 3 h). Both results were practically identical to the previous two time points. However, in group D there was a significant decrease (8.4 sec. compared to 22.1 at 3 h and 9.2 sec at baseline) with no statistical significance (P value=0.24). This decrease is a known phenomenon and is readily explained by the fact that most of the mice in group D remained for an extended time on the hot plate (3 h) and therefore may have some burns on their paws, causing over-sensitivity and therefore a much shorter WRL. This explanation of the reduced WRL in group D is supported by the next measurement at 24 h (see below).

At this stage, half the mice from each group were sacrificed, ca. 3 mice, and the liver and brain of each animal were taken for pharmacodynamics tests (vide infra). At 24 h after drug administration, 3 animals from each group were evaluated. The average WRL was 5.8 sec, for group A (very low value, about 50% less than baseline), 10.27 sec, for group C and 20.8 sec, for group D.

It was clear that the synthetic material $CD_3$-($8D_2$)-THC, exhibited a stronger and longer lasting analgesic effect (even at 24 h after drug administration), compared to natural THC and morphine.

The two groups of lowered concentration from each drug, 4 mg/kg and 2 mg/kg (groups E+F and G+H, respectively) were also studied (Table 5). After drug administration was observed a mild increase of 23% in the WRL of THC in group E (12.48 sec. compared to 10.17 sec at baseline), while in group F a greater increasing of 68% was observed in the WRL of $CD_3$-($8D_2$)-THC (14.03 sec. compared to 8.33 sec at baseline). The calc. P value, at this stage, based on a T test was 0.056 for group E and 0.009 for group F. The latter result indicated an excellent statistical significance. At 3 h after drug administration, a significant decrease in the increasing of the average WRL in group E, i.e. +8% was observed, compared to +23% at 0.5 h, while in group F a very minor decrease in the increasing of the average WRL (+65%, compared to +68% at 0.5 h) (13.77 sec. compared to 8.33 sec at baseline) was observed. The calculated P value, at this stage, based on a T test was 0.376 for group E and 0.004 for group F. The latter result indicated an excellent statistical significance. At 6 h after drug administration, a significantly decreased level of WRL in group E (−12% compared to baseline) was noted. However, this was not corroborated by the average WRL of group F which experienced an increase (+85% compared to baseline) with no statistical significance (P value=0.29). The calculated P value, at this stage, based on a T test was 0.297 for group E and 0.009 for group F. The latter result indicated excellent statistical significance. It is also clear (Table 5) that 0.5 h after drug administration a very small decrease of 1% in the WRL of THC at group G was observed (7.38 sec. compared to 7.45 sec at baseline), while in group H a small increase of 3%. in the WRL of $CD_3$-($8D_2$)-THC was noted (9.52 seconds compared to 9.23 seconds at baseline). The P value, at this stage, was 0.428 for group F, with no statistical significance. At 3 h. after drug administration, a significant increasing in the average WRL of group G, i.e. +31% was observed compared to the baseline (9.77 sec. compared to 7.45 sec at baseline), while in group H a mild increasing in the increasing WRL (+19%, compared to +3% at 0.5 h) was seen (10.97 sec. compared to 9.23 sec. at baseline). The calculated P value, at this stage, based on a T test was 0.109 for group E and 0.263 for group H, with no statistical significance. At 6 hours after drug administration, the same result in the average WRL of group G was observed, +31%, compared to baseline (9.77 sec. compared to 7.45 sec at baseline), while in group H there was a decrease in the increasing WRL (+9%, compared to +19% at 3 h) (10.07 sec. compared to 10.97 sec. at 3 h). The P value, at this stage, based on a T test was 0.091 for group G and 0.371 for group H, with no statistical significance.

For the lowest concentration of the administered drug, which was 2 mg/kg, no effect was observed at 0.5 h after drug administration for both THC and its deuterated derivative (7.38 seconds compared to 7.45 seconds at baseline for the former and 9.52 seconds compared to 9.23 sec at baseline for the latter). The calculated P value, for group F at this stage was 0.428, with no statistical significance.

At 3 h after drug administration, a significance increase in the average WRL of both group G, (+31% compared to baseline, 9.77 compared to 7.45 sec), and group H (+19% compared to baseline, 10.97 compared to 9.23 sec) was observed. The calculated P value at this stage, based on T test, was 0.109 for group E and 0.263 for group H, both with no statistical significance. Very similar results were observed 6 h after drug administration.

Greater activity of synthetic material 9D-THC was observed in comparison to the natural compound THC, at 3 h after administration of 4-8 mg/Kg.

Figure 11:
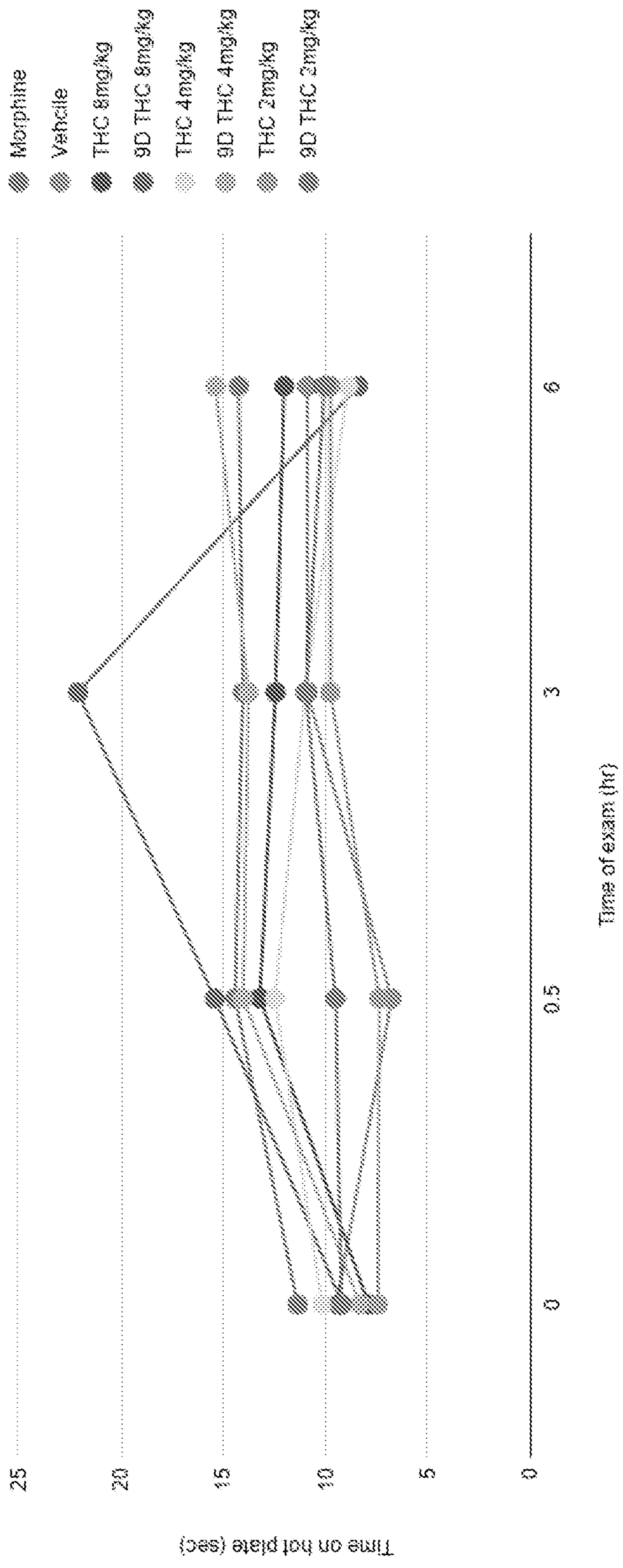
FIG. 11 shows line graphs summarizing hot plate experiments, showing mean time (in seconds) of mice on a hot plate as a function of time (0-6 hours) following the indicated treatments.
Figure 12:
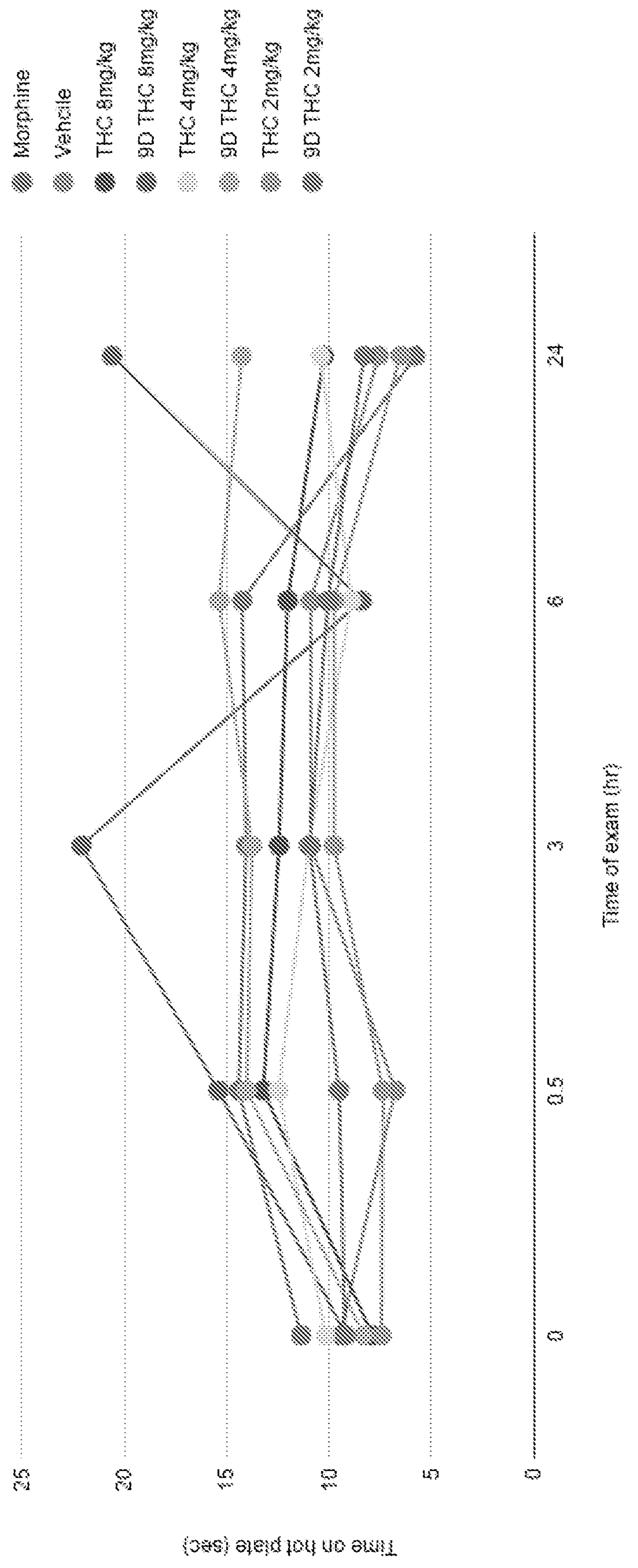
FIG. 12 Line graphs showing mean time (seconds) of mice on a hot plate as a function of time (0-24 hours) following the indicated treatments.

Expansion of time after testing the administered compound from 6 h (FIG. 11) to 24 h (FIG. 12) demonstrates the higher nociceptive activity of synthetic material 9D THC following extended time after administration.

In summary, it can be concluded that the deuterated derivative, 9-$CD_3$-($8D_2$)-THC, is much more effective in its analgesic activity in comparison to the natural THC, at a concentration range of 4-8 mg/kg and also much more effective in comparison to the popular drug morphine (which was administered at a concentration of 5 mg/kg). As abovementioned, body temperature was measured using a digital rectal thermometer immediately to prior each hot plate experiment. As apparent from Table 6 (vide infra), the lowest concentration of administered drug (2 mg/kg, groups G+H) was associated with a minor effect on the body temperature, in accordance with the hot plate experiment. At the medium concentration of 4 mg/kg (groups E+F), a very clear hypothermia effect associated with both materials was obtained, with the synthetic material being more effective than natural THC at all time points. Additionally, the results obtained from the synthetic THC derivative exhibit greater statistical significance (P value<0.02).

At the high concentration of 8 mg/kg (groups C+D), a strong effect was observed that was not trivially understood. In THC, the strongest effect was obtained at 0.5 h after drug administration, which decreased but did not vanish, while in the synthetic material exhibited its strongest effect is at 3 h, after which it decreased.

These experiments were further developed by creation of a hyperthermia effect using LPS in treated mice.

Thus, in general, both nociception and hypothermia, exhibit the same trend, where the synthetic deuterated THC derivative is more effective and exhibits an effect with longer duration than its natural THC counterpart.

TABLE 6

Body temperature results, groups A-H.

| Group | Animal # | Drug | t = 0 Temp. (°C) | t = 0 Avg. 6 mice | t = 0.5 h Temp. (°C) | t = 0.5 h Avg. 6 mice | t = 0.5 h Avg. change compared to t = 0 | t = 3 h Temp. (°C) | t = 3 h Avg. 6 mice | t = 3 h Average change compared to t = 0 | t = 6 h Temp. (°C) | t = 6 h Avg. 6 mice | t = 6 h Average change compared to t = 0 | t = 24 h Temp. (°C) | t = 24 h Avg. 6 mice | P value (rel. t = 0) t = 0.5 h | P value (rel. t = 0) t = 3 h | P value (rel. t = 0) t = 6 h | P value (rel. t = 0) t = 24 h |
|---|---|---|---|---|---|---|---|---|---|---|---|---|---|---|---|---|---|---|---|
| A | 1 | Morphine | 38.2 | 38.0 | 36.6 | 37.1 | −0.9 | 35.9 | 36.8 | −1.2 | 36.4 | 36.7 | −1.3 | 37.8 | 38.3 | 0.044 | 0.009 | 0.010 | 0.383 |
| | 2 | | 37.9 | | 36.7 | | | 36.8 | | | 36.4 | | | 37.8 | | | | | |
| | 3 | | 38.5 | | 39.2 | | | 36.9 | | | 36.8 | | | 39.4 | | | | | |
| | 4 | | 38.2 | | 38.0 | | | 37.0 | | | 36.0 | | | — | — | | | | — |
| | 5 | | 37.8 | | 37.0 | | | 37.7 | | | 37.1 | | | | | | | | |
| | 6 | | 37.1 | | 35.0 | | | 36.7 | | | 37.4 | | | | | | | | |
| B | 7 | Vehicle | 37.4 | 37.1 | 38.4 | 37.0 | −0.1 | 38.0 | 37.9 | +0.8 | 36.8 | 37.3 | +0.2 | 38.2 | 38.0 | 0.491 | 0.012 | 0.227 | 0.025 |
| | 8 | | 37.1 | | 37.9 | | | 37.8 | | | 36.7 | | | 37.7 | | | | | |
| | 9 | | 36.9 | | 34.0 | | | 37.7 | | | 37.2 | | | 38.2 | | | | | |
| | 10 | | 36.3 | | 37.1 | | | 38.3 | | | 37.7 | | | — | | | | | — |
| | 11 | | 36.9 | | 38.5 | | | 38.1 | | | 37.7 | | | | | | | | |
| | 12 | | 37.7 | | 36.3 | | | 37.7 | | | 37.7 | | | | | | | | |
| C | 13 | THC | 37.9 | 37.8 | 37.1 | 35.7 | −2.1 | 38.3 | 36.6 | −1.2 | 36.2 | 36.6 | −1.2 | 37.5 | 37.2 | 0.065 | 0.081 | 0.052 | 0.059 |
| | 14 | 8 mg/kg | 38.3 | | 36.4 | | | 36.1 | | | 36.2 | | | 36.9 | | | | | |
| | 15 | | 39.2 | | 37.9 | | | 37.7 | | | 36.4 | | | 37.1 | | | | | |
| | 16 | | 38.9 | | 31.7 | | | 35.1 | | | 36.4 | | | — | | | | | — |
| | 17 | | 36.6 | | 38.1 | | | 38.0 | | | 37.3 | | | | | | | | |
| | 18 | | 36.1 | | 32.8 | | | 34.3 | | | 36.8 | | | | | | | | |
| D | 19 | THC-d5 | 37.5 | 37.9 | 38.0 | 36.5 | −1.4 | 36.2 | 35.3 | −2.6 | 37.5 | 37.2 | −0.7 | 37.5 | | 0.015 | 0.001 | 0.018 | 0.250 |
| | 20 | 8 mg/kg | 37.8 | | 36.4 | | | 36.1 | | | 36.8 | | | died | | | | | |
| | 21 | | 38.5 | | 37.4 | | | 35.5 | | | 36.9 | | | 38.1 | | | | | |
| | 22 | | 38.2 | | 36.9 | | | 34.8 | | | 37.0 | | | — | | | | | — |
| | 23 | | 37.7 | | 34.8 | | | 34.0 | | | 37.5 | | | | | | | | |
| | 24 | | 37.6 | | 35.5 | | | 34.9 | | | 37.2 | | | | | | | | |
| E | 25.0 | THC | 36.6 | 37.8 | 37.9 | 36.8 | −1.0 | 36.8 | 37.5 | −0.3 | 36.6 | 37.1 | −0.7 | 37.0 | 37.3 | 0.160 | 0.285 | 0.071 | 0.365 |
| | 26.0 | 4 mg/kg | 38.1 | | 34.4 | | | 36.6 | | | 36.6 | | | 37.7 | | | | | |
| | 27.0 | | 37.5 | | 36.8 | | | 37.8 | | | 37.2 | | | 37.2 | | | | | |
| | 28.0 | | 37.9 | | 36.1 | | | 37.6 | | | 36.5 | | | — | | | | | — |
| | 29.0 | | 38.5 | | 36.4 | | | 37.6 | | | 37.0 | | | | | | | | |
| | 30.0 | | 37.9 | | 39.4 | | | 38.8 | | | 38.6 | | | | | | | | |
| F | 31.0 | THC-d5 | 37.0 | 37.8 | 37.8 | 36.7 | −1.1 | 36.7 | 37.2 | −0.6 | 35.8 | 36.5 | −1.3 | 37.6 | 37.3 | 0.117 | 0.030 | 0.001 | 0.249 |
| | 32.0 | 4 mg/kg | 38.5 | | 39.0 | | | 38.5 | | | 36.4 | | | 37.0 | | | | | |
| | 33.0 | | 37.9 | | 33.2 | | | 36.3 | | | 36.2 | | | 37.3 | | | | | |
| | 34.0 | | 38.1 | | 36.2 | | | 37.0 | | | 36.6 | | | — | | | | | — |
| | 35.0 | | 37.7 | | 36.6 | | | 37.1 | | | 36.8 | | | | | | | | |
| | 36.0 | | 37.5 | | 37.2 | | | 37.4 | | | 37.0 | | | | | | | | |
| G | 37.0 | THC | 37.4 | 37.4 | 38.2 | 38.1 | +0.7 | 36.6 | 37.7 | +0.3 | 36.2 | 36.8 | −0.6 | 37.4 | 38.1 | 0.009 | 0.213 | 0.034 | 0.143 |
| | 38.0 | 2 mg/kg | 37.0 | | 37.5 | | | 37.9 | | | 37.4 | | | 38.4 | | | | | |
| | 39.0 | | 38.2 | | 39.1 | | | 39.2 | | | 36.8 | | | 38.6 | | | | | |
| | 40.0 | | 37.2 | | 38.3 | | | 37.2 | | | 37.1 | | | — | | | | | — |

TABLE 6-continued

Body temperature results, groups A-H.

| | | | | | | | | | | | | | | | | | | | | |
|---|---|---|---|---|---|---|---|---|---|---|---|---|---|---|---|---|---|---|---|---|
| | 41.0 | | 37.1 | | 36.9 | | | 37.3 | | | 36.2 | | | | | | | | | |
| | 42.0 | | 37.7 | | 38.8 | | | 37.8 | | | 37.0 | | | | | | | | | |
| H | 43.0 | THC-d5 | 37.5 | 37.3 | 37.3 | 37.6 | +0.3 | 36.5 | 36.9 | −0.4 | 37.5 | 36.1 | −1.2 | 37.2 | | 37.1 | 0.132 | 0.166 | 0.126 | 0.339 |
| | 44.0 | 2 mg/kg | 36.9 | | 37.0 | | | 36.4 | | | 36.4 | | | 37.1 | | | | | | |
| | 45.0 | | 36.5 | | 37.8 | | | 37.1 | | | 37.1 | | | 36.9 | | | | | | |
| | 46.0 | | 38.8 | | 38.7 | | | 37.3 | | | 33.1 | | | | — | | | | | — |
| | 47.0 | | 36.8 | | 36.8 | | | 36.9 | | | 36.1 | | | | | | | | | |
| | 48.0 | | 37.1 | | 37.8 | | | 37.3 | | | 36.2 | | | | | | | | | |

Example 17. Pharmacokinetics

The pharmacokinetics of 9-$CD_3$-(8-$D_2$)-THC compared to natural THC was evaluated using both intraperitoneal i.p. injection and an oral gavage administration for each material. The mice were divided into four groups containing 6 mice (24 mice total). For each group of mice, a blood sample was withdrawn at baseline (t=0), and half-hour intervals (t=0.5, 2 and 5 h) after administration of the drug. Three mice, half of each group, were euthanized with CO2 after 5 h and their organs (brain and liver) were collected. From the second half of each group, another blood sample was withdrawn 24 h after administration, and then these animals were euthanized and the brain and liver were collected for analysis.

The results summarized in Tables 7-9 are presented as the percentage of injected material, found in the blood or in the organs of the mice.

TABLE 7

Pharmacokinetics of THC and 9-$CD_3$-(8-$D_2$)-THC in the blood, 0.5 h after i.p. injection

| Components [ng/mL] | mouse 1 | mouse 2 | mouse 3 | mouse 4 | mouse 5 | mouse 6 | Average |
|---|---|---|---|---|---|---|---|
| THC | | | | | | | |
| THC | 76.79 | 81.87 | 49.48 | 64.38 | 53.78 | 53.90 | 63.37 |
| 11-OH-THC | 2.40 | 2.44 | 2.10 | 3.43 | 2.27 | 2.37 | 2.50 |
| 11-COOH-THC | 30.26 | 22.27 | 20.76 | 32.18 | 25.30 | 19.81 | 25.10 |
| 9-$CD_3$-(8-$D_2$)-THC [THC-d5] | | | | | | | |
| THC-d5 | 183.41 | 93.82 | NA | 140.75 | 74.12 | 58.86 | 110.19 |
| 11-OH-THC-d5 | NA | NA | NA | NA | NA | NA | |
| 11-COOH-THC-d5 | NA | NA | NA | NA | NA | NA | |

TABLE 8

Pharmacokinetics of THC and 9-$CD_3$-(8-$D_2$)-THC in the liver, 5 h after oral gavage administration

| Components [ng/mL] | mouse 1 | mouse 2 | mouse 3 | Average |
|---|---|---|---|---|
| THC | | | | |
| THC | 1.41 | 4.94 | 4.97 | 3.77 |
| 11-OH-THC | 6.56 | 23.90 | 2.83 | 11.10 |
| 11-COOH-THC | 38.89 | 33.82 | 25.34 | 32.68 |
| 9-$CD_3$-(8-$D_2$)-THC [THC-d5] | | | | |
| THC-d5 | 5.57 | 6.28 | 6.13 | 5.99 |
| 11-OH-THC-d5 | 1.92 | NA | NA | |
| 11-COOH-THC-d5 | NA | NA | NA | |

TABLE 9

Pharmacokinetics of THC and 9-$CD_3$-(8-$D_2$)-THC in the liver, 24 h after i.p. injection

| Components [ng/mL] | mouse 1 | mouse 2 | mouse 3 | Average |
|---|---|---|---|---|
| THC | | | | |
| THC | 5.55 | 8.46 | 8.86 | 7.62 |
| 11-OH-THC | 0.37 | 3.12 | 1.46 | |
| 11-COOH-THC | NA | NA | 1.49 | |

TABLE 9-continued

Pharmacokinetics of THC and 9-$CD_3$-(8-$D_2$)-THC in the liver, 24 h after i.p. injection

| Components [ng/mL] | mouse 1 | mouse 2 | mouse 3 | Average |
|---|---|---|---|---|
| 9-$CD_3$-(8-$D_2$)-THC [THC-d5] | | | | |
| THC-d5 | 12.36 | 14.96 | 4.64 | 10.65 |
| 11-OH-THC-d5 | NA | NA | NA | |
| 11-COOH-THC-d5 | NA | NA | NA | |

As shown in Table 7, at 0.5 h after i.p. administration of THC, the average (n=6) concentration of THC in the blood was 63.37 ng/ml, while the corresponding average (n=5) blood concentration of 9-CD3-(8-D2)-THC was 110.19 ng/ml, which is 1.87 times higher. Another important result is that no 11-OH THC-d5 was observed at this evaluation, which may reinforce the isotopic effect theory, that the metabolism of the parent drug is slowed down.

This pharmacokinetic profile was also observed in the liver, at 5 h after oral gavage administration and following euthanasia (Table 8). Specifically, for THC, an average (n=3) of 3.77 ng/g was observed, while the corresponding average (n=3) liver concentration of 9-CD3-(8-D2)-THC was 5.99 ng/g, which is 1.59 times more.

Another set of observations were the concentrations in the liver, at 24 h after an i.p. administration following euthanasia. An average (n=3) of 7.62 ng/g for THC, was obtained, and an average (n=3) of 10.65 ng/g for 9-CD3-(8-D2)-THC, which was 1.40 times more (Table 9).

Example 18: Persistence of THC Derivatives in Mice Over Time

Blood samples from each mouse were collected at each time point for the pharmacokinetics tests. For 6 h after administrating of all tested drugs, and after testing their WRL on the hot plate, half the mice (n=3) of each group were sacrificed, and the liver and brain of each animal were taken for pharmacokinetics tests. From the remaining mice, blood samples were acquired at 12 h after administration for pharmacokinetics tests. At 24 h after drug administration, and after checking the WRL again, second half of each group of mice were sacrificed, and the liver and brain of each animal were taken for pharmacokinetics tests. All the results of the blood samples, which were taken through the 24 h of the experiment, are summarized in tables 10-12.

TABLE 10

Average results [ng/mL] - blood samples, at 8 mg/kg administration.
(In parentheses, number of mice taken out of total mice)

| | Administration Amount 8 mg/kg Time [h] | | | | |
|---|---|---|---|---|---|
| | 0.5 | 3 | 6 | 12 (3 mice) | 24 (3 mice) |
| THC | 14.34 | 6.53 (5/6) | 4.14 (4/5) | 0.81 | 0.26 |
| 11-OH-THC | 1.96 (5/5) | 0.44 (3/3) | NA | NA | NA |
| 11-COOH-THC | 15.85 (5/5 | 3.44 | 3.57 | 1.89 (1/1) | NA |
| THC-d5 | 22.5 (6/6) | 7.27 (5/5) | 1.81 (1/1) | 0.15 | NA |
| 11-OH-THC-d5 | 8.50 (5/5) | 10.03 (5/5) | 0.16 (2/6) | NA | NA |
| 11-COOH-THC-d5 | 25.85 (6/6) | 25.34 (6/6) | 11.71 (5/6) | 8.73 | 0.10 (1/1) |

TABLE 11

Average results [ng/mL] - blood samples, at 4 mg/kg administration

| | Administration amount 4 mg/kg Time [h] | | | | |
|---|---|---|---|---|---|
| | 0.5 | 3 | 6 | 12 (3 mice) | 24 (3 mice) |
| THC | 10.49 (3/6) | 2.78 (4/6) | 2.44 (5/5) | NA | 0.25 (2/2) |
| 11-OH-THC | 1.54 (5/5) | 0.18 (2/2) | NA | NA | NA |
| 11-COOH-THC | 11.87 (6/6) | 1.39 (4/4) | 0.41 (2/2) | NA | NA |
| THC-d5 | 10.41 (5/6) | 1.44 (4/4) | NA | NA | NA |
| 11-OH-THC-d5 | 4.70 (4/4) | NA | NA | NA | NA |
| 11-COOH-THC-d5 | 18.54 (6/6) | 6.00 (5/5) | 0.14 (1/1) | NA | NA |

All the results of the brain and liver samples, which were taken postmortem 6 h or 24 h after administration (n=3) are summarized in Tables 12-13.

TABLE 12

Average results [ng/g] for 3 mice in every group - brain samples

| | Administration amount | | | | | |
|---|---|---|---|---|---|---|
| | 8 mg/kg | | 4 mg/kg | | 2 mg/kg | |
| | died at 6 h | died at 24 h | died at 6 h | died at 24 h | died at 6 h | died at 24 h |
| THC | 16.88 (2) | NA | NA | 14.10 (1) | NA | NA |
| 11-OH-THC | 5.2 (2) | NA | NA | NA | NA | NA |
| 11-COOH-THC | 2.04 (1) | NA | NA | NA | NA | NA |
| THC-d5 | 48.0 (2) | NA (2) | NA | NA | NA | NA |
| 11-OH-THC-d5 | 29.44 | 3.54 (2) | NA | NA | NA | NA |
| 11-COOH-THC-d5 | 17.81 | 37.05 (1) | NA | NA | 1.62 (1) | NA |

TABLE 13

Average results [ng/g] for 3 mice in every group - brain samples

| | Administration amount | | | | | |
|---|---|---|---|---|---|---|
| | 8 mg/kg | | 4 mg/kg | | 2 mg/kg | |
| | died at 6 h | died at 24 h | died at 6 h | died at 24 h | died at 6 h | died at 24 h |
| THC | 11.08 | 3.52 | 11.40 | 0.87 | 9.18 | 0.74 (2/3) |
| 11-OH-THC | 22.94 | 5.57 (1) | 41.89 | NA | 8.76 | NA |
| 11-COOH-THC | 60.95 | NA | 46.06 | 2.89 (1) | 3.83 | NA |

TABLE 13-continued

| Average results [ng/g] for 3 mice in every group - brain samples | | | | | | |
|---|---|---|---|---|---|---|
| | Administration amount | | | | | |
| | 8 mg/kg | | 4 mg/kg | | 2 mg/kg | |
| | died at 6 h | died at 24 h | died at 6 h | died at 24 h | died at 6 h | died at 24 h |
| THC-d5 | 57.83 | 1.64 (2) | 16.07 | NA | 3.31 | 0.75 |
| 11-OH-THC-d5 | 38.28 | 0.30 (2) | 38.42 | 5.9 | 5.84 | 5.45 (1) |
| 11-COOH-THC-d5 | 66.90 | NA | 42.31 | 8.66 (2) | 17.33 | NA |

As evident from Table 12, after 24 h after administration there is evidence for the synthetic material in the brain—in the highest concentration of 8 mg/kg, whereas both the natural material and its metabolites were absent. At 6 h after administration, there was a significant difference in the mean result of THC-$d_5$ compared to THC. The latter two discoveries are explained by the fact that the synthetic material remains much more time in the brain due to its slower metabolism. This is in correlation with the enhanced biological activity of analgesic effects.

From Table 13, at 6 h after administration there was noticed a significant difference in the mean result of THC-$d_5$ in comparison with THC. Also observed was a tendency of decreasing of the THC or THC-$d_5$ concentration in the liver over time, for each compound and in each concentration of administration.

In conclusion, the 9-$CD_3$-(8-$D_2$)-THC THC derivative, disclosed herein, in accordance with some embodiments, exhibits better metabolic stability than THC.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

The invention claimed is:

1. A THC derivative having the structure of Formula I:

(I)

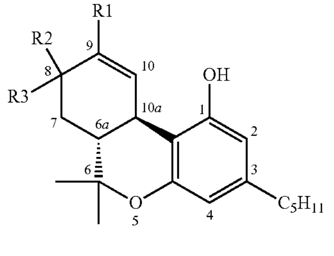

or enantiomer, acid, ester, a pharmaceutically acceptable salt, or prodrug thereof, wherein:

R1 is a substituted methyl group $CX_3$ wherein X is fluorine; and R2 and R3, independently, are selected from hydrogen and deuterium.

2. The THC derivative of claim 1, wherein, when X is fluorine, each of R2 and R3 are hydrogen atoms.

3. A pharmaceutical composition comprising the THC derivative of claim 1.

4. A pharmaceutical composition comprising a THC derivative having the structure of Formula II:

(II)

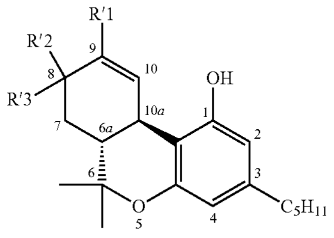

or enantiomer, acid, ester, or a pharmaceutically acceptable salt, or prodrug thereof, wherein the compound comprises substituents R'1, R'2 and R'3 as shown in Formula (II), wherein R'1 is selected from a hydrogen and a substituted methyl group $CX_3$ where X is fluorine; R'2 is hydrogen or deuterium; and R'3 is hydrogen or deuterium.

5. The pharmaceutical composition of claim 4, wherein each of R'1, R'2 and R'3 is a hydrogen.

6. The pharmaceutical composition of claim 4, wherein R'1 is a substituted methyl group $CX_3$ where X is fluorine.

7. The pharmaceutical composition of claim 6, wherein each of R'2 and R'3 is hydrogen.

8. The pharmaceutical composition of claim 4, in a dosage oral form, for parenteral or for enteral use.

9. The pharmaceutical composition of claim 8, for treatment or prevention of a disease or disorder wherein the disease or disorder is selected from pain, neurodegenerative diseases or disorders and insomnia.

10. A method of treating or preventing a disease or disorder, the method comprising administering to a subject in need thereof a pharmaceutical composition comprising the pharmaceutical composition of claim 4, wherein the disease or disorder is at least one of pain, neurodegenerative disease or disorder and insomnia.

11. The method of claim 10, wherein said administering comprises administering via a route of administration selected from the group consisting of oral administration, parenteral administration, enteral administration and intravenous administration.

12. A process of synthesizing 9-CD3-(8-D2)-THC, the process comprises the steps of:

coupling (1R,6R)-6-(1-Hydroxy-1-methylethyl)-cyclohex-2-en-1-[(1,1-dimethylethyl)dimethylsilyloxy)]-4-

(methyl-$d_3$)-5-$d_2$ (compound 15) with olivetol to provide 1,3-Dihydroxy-2-((1R,6R)-6-(1-Hydroxy-1-methylethyl)-4-(methyl-$d_3$)-5-$d_2$-cyclohex-2-en-1-yl)-5-pentylbenzene (compound 17); and cyclization of 1,3-Dihydroxy-2-((1R,6R)-6-(1-Hydroxy-1-methylethyl)-4-(methyl-$d_3$)-5-$d_2$-cyclohex-2-en-1-yl)-5-pentylbenzene (compound 17) to provide 9-CD3-(8-D2)-THC.

13. The process of claim 12, wherein (1R,6R)-6-(1-Hydroxy-1-methylethyl)-cyclohex-2-en-1-[(1,1-dimethylethyl)dimethylsilyloxy)]-4-(methyl-$d_3$)-5-$d_2$ (compound 15) is produced according to a process comprising the steps of:

reduction 4,4,4-$d_3$, 3-(methyl-$d_3$)-2-Butenoic acid-ethyl ester (compound 9) to the corresponding alcohol-4,4,4-$d_3$, 3-(methyl-$d_3$)-2-Buten-1-ol (compound 10);

mild oxidation of alcohol-4,4,4-$d_3$, 3-(methyl-$d_3$)-2-Buten-1-ol (compound 10) to give 4,4,4-$d_3$, 3-(methyl-$d_3$)-2-Butenal (compound 11);

reacting 4,4,4-$d_3$, 3-(methyl-$d_3$)-2-Butenal-(compound 11) with t-butyldimethylchloro silane under basic conditions to produce (1,1-dimethylethyl)dimethyl[(4,4-$d_2$, 3-(methyl-$d_3$)-1,3-butadien-1-yl)oxy]-Silane (compound 12);

reacting 3-propenoyl-2-oxazolidinone (compound 4) with (1,1-dimethylethyl)dimethyl[(4,4-$d_2$, 3-(methyl-$d_3$)-1,3-butadien-1-yl)oxy]-Silane-(compound 12) in the presence of a chiral catalyst to produce 3-[(1R,2R)-2-((1,1-dimethylethyl)dimethylsilyloxy)-4-(methyl-$d_3$)-5-$d_2$-cyclohex-3-en-1-ylcarbonyl]-2-oxazolidinone (compound 13);

transesterification of 3-[(1R,2R)-2-((1,1-dimethylethyl)dimethylsilyloxy)-4-(methyl-$d_3$)-5-$d_2$-cyclohex-3-en-1-ylcarbonyl]-2-oxazolidinone (compound 13) to produce Benzyl-(1R,2R)-2-(1,1-dimethylethyl)dimethylsilyloxy)-4-(methyl-$d_3$)-5-$d_2$-cyclohex-3-en-1-carboxylate (compound 14); and Grignard reaction of Benzyl-(1R,2R)-2-(1,1-dimethylethyl)dimethylsilyloxy)-4-(methyl-$d_3$)-5-$d_2$-cyclohex-3-en-1-carboxylate (compound 14) to produce (1R,6R)-6-(1-Hydroxy-1-methylethyl)-cyclohex-2-en-1-[(1,1-dimethylethyl)dimethylsilyloxy)]-4-(methyl-$d_3$)-5-$d_2$ (compound 15).

14. A compound produced according to the process of claim 12.

15. A method of treating a disease or disorder, the method comprising administering to a subject in need thereof a pharmaceutical composition comprising the pharmaceutical composition of claim 1, wherein the disease or disorder is at least one of pain, neurodegenerative disease or disorder and insomnia.

* * * * *